(12) United States Patent
Grate et al.

(10) Patent No.: US 7,892,856 B2
(45) Date of Patent: Feb. 22, 2011

(54) FLOW-CONTROLLED MAGNETIC PARTICLE MANIPULATION

(75) Inventors: Jay W. Grate, West Richland, WA (US); Cynthia J. Bruckner-Lea, Richland, WA (US); David A. Holman, Las Vegas, NV (US)

(73) Assignee: Battelle Memorial Institute, Richland, WA (US)

( * ) Notice: Subject to any disclaimer, the term of this patent is extended or adjusted under 35 U.S.C. 154(b) by 721 days.

(21) Appl. No.: 11/646,216

(22) Filed: Dec. 26, 2006

(65) Prior Publication Data

US 2007/0105163 A1    May 10, 2007

Related U.S. Application Data

(62) Division of application No. 09/944,816, filed on Aug. 31, 2001, now abandoned.

(51) Int. Cl.
*G01N 33/53* (2006.01)
(52) U.S. Cl. .................... 436/526; 436/43; 436/45; 436/46; 422/31
(58) Field of Classification Search .......... 435/4, 435/287.1, 287.2, 287.3; 422/68.1, 82.05, 422/82.08, 186, 186.1; 436/518, 526
See application file for complete search history.

(56) References Cited

U.S. PATENT DOCUMENTS

| | | | | |
|---|---|---|---|---|
| 4,784,767 A | * | 11/1988 | Hasuda et al. | 210/222 |
| 5,601,988 A | * | 2/1997 | Gordon | 435/7.23 |
| 5,695,720 A | * | 12/1997 | Wade et al. | 422/82 |
| 6,432,630 B1 | * | 8/2002 | Blankenstein | 435/4 |

* cited by examiner

*Primary Examiner*—Jacob Cheu
*Assistant Examiner*—Pensee T Do
(74) *Attorney, Agent, or Firm*—Douglas E. McKinley, Jr.

(57) ABSTRACT

Inventive methods and apparatus are useful for collecting magnetic materials in one or more magnetic fields and resuspending the particles into a dispersion medium, and optionally repeating collection/resuspension one or more times in the same or a different medium, by controlling the direction and rate of fluid flow through a fluid flow path. The methods provide for contacting derivatized particles with test samples and reagents, removal of excess reagent, washing of magnetic material, and resuspension for analysis, among other uses. The methods are applicable to a wide variety of chemical and biological materials that are susceptible to magnetic labeling, including, for example, cells, viruses, oligonucleotides, proteins, hormones, receptor-ligand complexes, environmental contaminants and the like.

44 Claims, 11 Drawing Sheets

FLOW-CONTROLLED MAGNETIC PARTICLE MANIPULATION

RELATED APPLICATIONS

This application is a divisional of U.S. patent application Ser. No. 09/944,816 filed Aug. 31, 2001, now abandoned.

GOVERNMENT RIGHTS STATEMENT

This invention was made with Government support under Contract Number DE-AC0676RLO1830 awarded by the U.S. Department of Energy. The Government has certain rights in the invention.

BACKGROUND OF THE INVENTION

The present invention relates to systems for the magnetic collection of magnetically-responsive particles (referred to herein as "magnetic particles"), and the subsequent controlled dispersion of the particles. In particular, the invention relates to the detection, isolation, separation and/or manipulation of target substances, such as for example, chemicals and/or biological substances such as biochemicals, cells, cell components, bacteria, viruses, toxins, nucleic acids, hormones, proteins, receptor-ligand complexes, other complex molecules, or combinations thereof, by selective interaction thereof with magnetic particles, which can be separated from a medium, and subsequently resuspended for further analysis, isolation or other use.

As a background to the invention, many techniques are known and used in the prior art that involve identification, separation, and/or manipulation of target entities, such as cells or microbes, within a fluid medium such as bodily fluids, culture fluids or samples from the environment. It is readily appreciated that such techniques often require multiple washing and binding steps. These steps are conducted in many such techniques by tedious manual pipetting and decanting procedures or by using automated robotic systems that are large and not field-portable. Such identification, separation and/or manipulation techniques may involve, for example, analyzing a sample to determine whether a specific pollutant, toxin or other substance is present and, if so, in what quantity; extracting a specific target substance, such as nucleic acid fragments, proteins, enzymes or the like from a sample for subsequent processing or utilization; or the like. It is readily appreciated that such techniques often must exhibit significant sensitivity, especially when the target substance is present in trace quantities, in order to provide accurate and useful information or to provide a suitable specimen in an isolation technique.

One example of a technique that involves separating, isolating or otherwise manipulating organic molecules in trace is an immunoassay technique using antibodies as the analytical reagents. The principle of immunoassays is well understood. Antibodies recognize a specific analyte by following specific interactions. For low molecular weight analytes such as drugs or metabolites, it is customary to perform competitive immunoassays. Typically, a fixed, limited quantity of specific antibody is allowed to incubate with a known concentration of labeled analyte and a sample possibly containing some unknown concentration of that analyte. The quantity of label bound to antibody is inversely proportional to the amount of analyte in the test specimen.

Although there is a high number of immunoassay techniques, only a few are widely used. Among these are indirect techniques where the analyte is measured through a label species conjugated with one of the immunoreagents. For quantitation, it is customary to perform a bound/free separation so that labeled analyte associated with the antibody can be detected. If one of the components of the immunologic reaction is immobilized on a solid phase (heterogeneous assay), the experimental procedure is simplified. A heterogeneous immunoassay that involves competitive binding of the analyte and an enzyme-labeled analyte to the antibody is called an Enzyme Linked Immunosorbent Assay (ELISA).

For analytes which have at least two distinguishable antigenic determinants, a simpler and more precise approach is to perform a sandwich immunoassay, which uses a first antibody directed to one antigenic site as a capture antibody and a second antibody directed at another characteristic determinant as the signal generating antibody. Thus, if the capture antibody is separated from solution, or bound on some solid support, the only way in which signal antibody can be bound to solid support or separated from solution is via analyte. The advantages of sandwich assay are that: (1) signal is directly proportional to analyte concentration on the low end of the analyte curve; (2) extreme sensitivity can be obtained on the low concentration end; (3) sandwich assays are assays of "excesses" since capture antibody and label antibody are typically in excess of analyte and so error is mainly related to accuracy of sample input; and (4) a wide dynamic analyte detection range (as much as 4-5 logs) is possible. Sandwich assay technology, like competitive assay, employ a wide range of systems for performing bound/free separations. Typically in such assays, antibodies for the analytes of interest are placed with great precision on a solid support so as to permit analyte binding to take place on the bound antibodies. Next, solution is added which causes unbound and non-specifically bound analyte to be carried from the binding region. Then a second labeled antibody is added, and solution is added to wash away the unbound secondary antibody. If the secondary antibody is enzyme labeled, then enzyme substrates are added to result in a detectable signal (e.g. color change, fluorescence, conductivity change) which will be proportional to the quantity of enzyme (and therefore analyte) specifically bound.

There are numerous ways for performing the bound/free separation utilizing a specific binding substance immobilized on a solid phase, such as, for example, antibody adsorbed or covalently linked to the inside of a tube (coated tube assay), or, more recently, affixed to a mobile solid phase, such as, for example, elongate structures that can be submerged in a liquid and then withdrawn, or beads, which can either be centrifuged or separated with filters or magnetically. Typically, a separation system should have the characteristics that the separation can easily be performed, excess reagent rates for DNA hybridization and elution, as well as for DNA amplification using polymerase chain reaction (PCR) or other enzyme amplification methe.

Detection of signal or radiant-energy response in an assay such as those discussed above may be accomplished through a variety of techniques. One example is fluorescent detection of a fluorescently labeled antibody, analyte or other small molecule that could be associated with the analyte. Radioactive detection is also a possibility if system components are impervious to the type of radioactive emission detected. Colorimetric detection of a dye attached to the antibody or analyte, possibly enclosed in a liposome, is also possible. Chemiluminescent, bioluminescent, electrochemiluminescent, or enzymatic detection is also possible, provided the substrate for the detection reaction become available after the bound/free separation. Thus, a variety of methods exist to obtain a readable signal or other radiant-energy response.

One major challenge in the use of immobilized binding substances is the limited lifetime of a chemically selective surface, especially those that include biomolecules (often referred to as "biosensors"). Many biomolecules in aqueous solution at room temperature will chemically degrade over time and typically have a lifetime ranging from only hours up to about 1 week. Therefore, it is not feasible to keep a biosensor surface immersed in aqueous solution continuously for long periods of use. The solution composition also effects the lifetime of biosensors. The structure and function of biomolecules and biological materials are sensitive to environmental conditions such as salt concentration, pH and temperature. Changes in solution composition and temperature can irreversibly denature proteins so that they will no longer bind to specific ligands. The use of whole cells in sensor systems is also challenging since cells require the correct mix of metabolites to remain viable, and solution composition and solution flow rate effect the growth rate of viable cells. The specificity and therefore irreversible nature of many biospecific interactions also contributes to the limited lifetime of biosensing surfaces. Selective interactions such as antibody-antigen interactions are essentially irreversible over the time course of minutes. Harsh reagents may be used to remove bound antigens (and non-specifically bound molecules); however, this decreases the subsequent binding activity of the antibody itself so that the regenerated sensing surface is not as effective as the fresh sensing surface, negatively impacting assay accuracy and reliability. In addition, the lifetime of a biosensor is often also limited due to "fouling" of the sensor surface caused by the non-specific binding of materials in a sample matrix onto the biosensor surface.

These problems have resulted in increased use of renewable surfaces for biosensing in which the chemically selective chemistry is on the surface of small particles. Fresh aliquots of derivatized particles can therefore be used for each analysis. After such an analysis, the derivatized particles can be flushed from the system and new particles are used for a subsequent analysis.

Where the derivatized particles are magnetic particles, isolation of the particles from media during analysis can be achieved using magnetic separation or high gradient magnetic separation (HGMS). As used herein, the term "magnetic" is intended to refer to a property of a particle whereby a force is exerted thereon by the application of a magnetic field thereto. In magnetic separation, particles of relatively larger size (i.e., about 0.5 microns or greater in diameter) are captured or separated and in HGMS, smaller particles, such as, for example, colloidal magnetic particles are separated.

Over the past several years, sub-millimeter-scale, automated flow-based analyzers and chemical detector arrays have steadily approached the technology level needed for commercialization. Development is continuing toward ever more compact diagnostic analyzers for automated immunoassays, DNA purification and amplification, cell separation, environmental contaminant detection and the like.

In light of this background, there remain needs for further development of systems for the magnetic collection of magnetic particles, and the subsequent controlled resuspension of the particles. In particular, a need exists for further development of systems for the specific detection, isolation, separation and/or manipulation of target substances by selective interaction thereof with magnetic particles, which can be separated from a medium, and subsequently resuspended for further analysis, isolation or other use. The present invention addresses these needs.

SUMMARY OF THE INVENTION

The present invention provides novel systems for conducting magnetic particle separations and resuspensions in one or more fluid media. In accordance with one aspect of the invention, magnetic particle capture and release are controlled by controlling the rate of fluid flow through a capture zone that passes through a fixed magnetic field. At low flow rates through the capture zone, the particles can be captured reproducibly and quantitatively. A high flow rate through the capture zone displaces the particles from the magnetic field.

The invention provides systems that facilitate isolation of target substances by providing methods for manipulating magnetic particles both during and after the binding of target substances onto the magnetic particles. The target substance can then be tested, if desired, using one or more detection or analysis systems, such as luminescence detectors, spectrophotometric analysis, fluorometers, mass spectrometers, flow cytometers, hematology analyzers, or other cell counting or analytical devices.

The term "target substance" as used herein, refers to a wide variety of substances of biological, medical or environmental interest which are measurable individually or as a group. Examples include cells, both eukaryotic (e.g., leukocytes, erythrocytes or fungi) and prokaryotic (e.g., bacteria, protozoa or mycoplasma), viruses, cell components, molecules (e.g., proteins), macromolecules (e.g., nucleic acids-RNA, DNA), and chemicals (e.g., pesticides, herbicides, explosives). Cell-associated target substances include, for example, components of the cell membrane, cytoplasm or nucleus. Among such cell-associated structures are membrane-bound proteins or glycoproteins, including cell surface antigens of either host cell or viral origin, histocompatibility antigens, or membrane receptors. These target substances may be bound as discrete entities or in the form of complexes or aggregates. Such separations are accomplished using methods of the invention which rely on the interaction of the binding substance with at least one characteristic target substance or analyte of interest.

Binding of the target substances to the magnetic particles is controlled by the surface chemistry of the magnetic particles. The chemistry of the magnetic particles may be used for binding target substances via non-specific interactions, such as, for example, electrostatic interactions, van der Waals interactions, dipole-dipole interactions and/or hydrogen bonding interactions. For example, where it is desired to isolate all or substantially all positively charged proteins in a sample, this can be accomplished in accordance with the invention using negatively charged magnetic beads. Similarly, positively charged magnetic beads can be used to bind all or substantially all DNA (which is negatively charged) in a sample. Alternatively, the magnetic particles may be chemically modified to include specific binding substances that interact selectively with the target substances. Representative examples of binding substances that can be used in accordance with the invention include antigens, antibodies, protein receptors, ligands, oligonucleotides, streptavidin, avidin, biotin and lectin. One class of specific binding substance that is used to selectively interact with the target substance is the class of antibodies capable of immunospecifically recognizing antigens. The term "antibody" as used herein includes immunoglobulins, monoclonal or polyclonal and immunoreactive immunoglobulin fragments. Thus, examples of characteristic target substances and their specific binding substances are: receptor-hormone, receptor-ligand, agonist-antagonist, RNA or DNA oligomers-complimentary sequences, Fc receptor of mouse IgG-protein A, avidin-biotin and virus-receptor. Still other specific binding pair combinations that may be determined using the methods of this invention will be apparent to those skilled in the art.

When used for immunoassay, the instant invention provides a highly sensitive, but relatively small-scale system for the collection of analyte. The speed and reproducibility of collection and resuspension are important features for automating all of the binding, washing, and mixing steps needed using small volumes to achieve a relatively low-cost test for analytes. When used for performing an immunoassay or other such analysis, the instant invention makes possible a significant reduction in volume for all types of samples, resulting in higher concentrations of the target entity, thus permitting shorter analysis time. This is achievable without the need for removing, reversing or minimizing the magnetic field used to capture the magnetic particles.

As such, according to one aspect of this invention, a method is provided for separating magnetic particles from a non-magnetic carrier medium containing the particles and then resuspending the separated magnetic particles in a suitable dispersion medium. The carrier medium and the dispersion medium can be the same or different. The method initially involves providing a fluid flow path that extends through a magnetic field source, and introducing the carrier medium/magnetic particle mixture into the fluid flow path. A magnetic field intercepts the fluid flow path and captures magnetic particles in the fluid flow path when the mixture flows through the capture zone at a predetermined capture rate. The magnetic particles are released only when the same or a different medium is caused to flow through the capture zone at a higher rate effective to move the particles from the capture zone.

A method in accordance with the invention includes: (1) providing a fluid flow path having first and second ends and a fluid flow controller effective to variably impose a positive or negative pressure on the flow path to cause controlled fluid flow through the fluid flow path in a first or second direction at predetermined rates, and a capture zone between the first and second ends, wherein a fixed magnetic field intercepts the fluid flow path in the capture zone; (2) providing in the fluid flow path a first mixture including a plurality of solid magnetic particles dispersed in a carrier medium; (3) passing the first mixture through the capture zone at a first predetermined capture rate whereby a major portion of the magnetic particles become trapped in the capture zone by the force of the magnetic field and thereby separated from the carrier medium to form a first magnetic particle isolate; (4) perfusing the first magnetic particle isolate with a first dispersion medium; and (5) pulsing the first dispersion medium through the capture zone at a first predetermined dispersion rate effective to dislodge the first magnetic particle isolate from the capture zone, move the magnetic particles from the magnetic field, and suspend the magnetic particles in the first dispersion medium to provide a second mixture. If desired, the magnetic particles can be captured and released multiple times. This procedure can be used to enhance mixing and therefore molecular capture efficiency from a small fluid volume. In addition, the same fluid can be used as the carrier medium and the dispersion medium. Thus, the first and second mixtures can be the same. The capture and release can occur within the same volume of fluid by reversing the fluid flow direction through the capture zone during the capture and release functions. Alternatively, the capture and release can be into fresh volumes of fluid that are moved through the capture zone.

According to another aspect of the present invention, there is provided an apparatus for separating magnetic particles from a non-magnetic fluid medium containing such particles. The apparatus includes: (1) a fluid flow path, the fluid flow path having first and second ends and a capture zone between the first and second ends; (2) a fluid flow controller effective to variably impose a positive or negative pressure on the flow path to cause controlled fluid flow through the fluid flow path in a first or second direction at predetermined rates; (3) a magnetic field source generating a fixed magnetic field, the source positioned in a fixed relationship to the fluid flow path whereby the field intercepts the fluid flow path in the capture zone; and (4) a detector positioned to detect a physical or chemical property of a fluid in the flow path.

It is an object of the invention to provide novel systems and methods for capturing and resuspending magnetic particles that provide alternatives to systems and methods of the prior art.

Further forms, embodiments, objects, advantages, benefits, aspects and features of the present invention will be apparent from the drawings and detailed description herein.

BRIEF DESCRIPTION OF THE FIGURES

Although the characteristic features of this invention will be particularly pointed out in the claims, the invention itself, and the manner in which it may be made and used, may be better understood by referring to the following descriptions taken in connection with the accompanying figures forming a part hereof.

DESCRIPTION OF PREFERRED EMBODIMENTS

For the purposes of promoting an understanding of the principles of the invention, reference will now be made to preferred embodiments and specific language will be used to describe the same. It will nevertheless be understood that no limitation of the scope of the invention is thereby intended, such alternations and further modifications in the invention, and such further applications of the principles of the invention as described herein being contemplated as would normally occur to one skilled in the art to which the invention pertains.

The invention encompasses fluid flow systems for separating magnetic particles from a fluid medium, and resuspending the particles one or more times in the same or different media, by controlling the rates of fluid flow through a capture zone. In accordance with the invention, a magnetic field intercepts the fluid flow path in the capture zone to effect separation. The magnetic field in certain preferred embodiments is a fixed magnetic field, which term is used herein to refer to a magnetic field that remains substantially unchanged during capture and resuspension of magnetic particles. In certain embodiments, the fixed magnetic field is provided by positioning a permanent magnet in a fixed relationship to the fluid flow path. This relationship can be achieved, for example, by affixing the permanent magnet directly to a conduit defining the flow path, or alternatively by affixing the permanent magnet to a structure that does not move in relation to the flow path. In other embodiments, the fixed magnetic field is provided by an electromagnet that is positioned in a fixed relationship to the fluid flow path and that is configured to generate a magnetic field having a substantially constant field strength during capture and resuspension of magnetic particles in an inventive system.

Inventive systems have extensive utility for performing procedures which call for not only separation of magnetic particles from a medium, but also the resuspension of the particles in the same or different media in one or more subsequent steps. By controlling the selection of fluids for entry into the fluid flow path and the rates and directions of fluid flow, inventive systems find advantageous use in a wide variety of assays and other techniques that require substrates to be contacted with various fluids in a predetermined sequence. The present invention is particularly well suited for use in connection with automated fluid flow systems such as, but not limited to, procedures referred to as Sequential Injection Analysis (SIA) procedures. By automating an inventive fluid flow separation system, precise measurements may be obtained quickly and in a repeatable manner using relatively small amounts of reagents and other materials.

Figure 1:
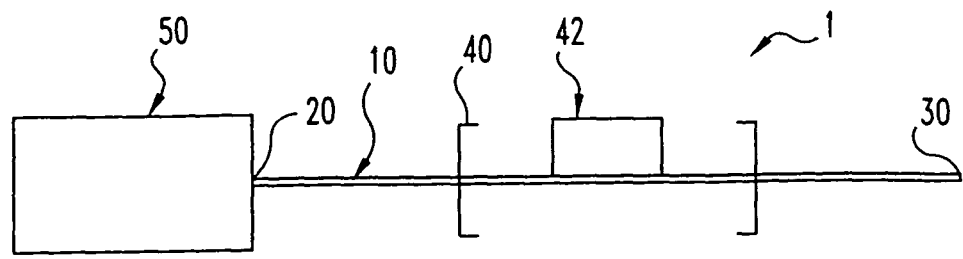
FIG. 1 is a schematic view of a first embodiment of a system in accordance with the invention.

Referring to FIG. 1, system 1 includes fluid flow path 10, having a first end 20 and a second end 30, and fluid flow controller 50. System 1 also includes capture zone 40 between first end 20 and second end 30. Capture zone 40 is distinguished from the remainder of flow path 10 in that a magnetic field intercepts fluid flow path 10 in capture zone 40. The magnetic field is provided by positioning a magnetic field source 42 in a fixed relationship to flow path 10. Controller 50 is effective to variably impose a positive or negative pressure on the flow path to cause controlled fluid flow through fluid flow path 10 in a first or second direction at varying rates. Controller 50 in certain embodiments is also configured to aspirate media into flow path 10 from different sources. Flow path 10 can be defined by a tube, as in the embodiments described in the Examples, or can alternatively be a microchannel. Microchannels, which often have internal diameters of less than about 100 microns, can be formed, for example, by machining, microfabrication or molding techniques known in the art. Processes and techniques for forming a microchannel are described, for example, in U.S. Pat. Nos. 5,611,214, 5,811,062, 6,129,973, 6,192,596 and 6,200,536.

In a manner of using system 1, a first mixture is provided in the flow path, the mixture including a plurality of solid magnetic particles dispersed in a carrier medium. The first mixture, which can also be referred to as a suspension or a slurry, can be provided in the flow path in a wide variety of ways, nonlimiting examples of which are provided in more detail below. Once the first mixture is positioned within fluid flow path 10, flow controller 50 exerts a positive or negative pressure on the mixture to cause the mixture to pass through capture zone 40 at a predetermined rate (referred to herein as a "capture rate") whereby a major portion of the magnetic particles become trapped in capture zone 40 by the force of the magnetic field, and thereby separated from the carrier medium to form a first magnetic particle isolate. The term "major portion" is used herein to refer to a portion necessary to achieve a desired result in a given separation procedure within acceptable ranges of precision. For example, when inventive systems are used to conduct an ELISA assay, examples of which is described in greater detail below, it is preferred that at least about 90% by weight, more preferably at least about 95%, of the magnetic particles are captured by the force of the magnetic field when the mixture passes through the capture zone to ensure assay results within an acceptable range of error. It is to be understood that different ranges of capture efficiency may be preferred when an inventive system is used in different types of procedures.

The predetermined capture flow rate is a flow rate sufficiently low that magnetic attractive forces on the particles in the mixture exceed viscous and gravitational forces imparted by movement of the carrier medium. At this flow rate, those particles are held, or captured, in the capture zone while the carrier fluid exits the capture zone. For example, in a system described in the example below in which the fluid flow path has an internal diameter of about 0.02 inch (~0.5 mm) and the particles are about 0.5 µm in diameter, a preferred capture flow rate is less than or equal to about 13 mm/s (2.5 µl/s). More preferably, the capture rate for this example is from about 1.0 to 13 mm/s. A person of ordinary skill in the art will readily recognize that the preferred rate may vary depending upon a variety of features of a given system, such as, for example, particle size, particle magnetic susceptibility, magnetic field strength, position of the magnetic field source, and flow path configuration (diameter, wall thickness, tubing or channel material, etc.), and will be able to make adjustments to the capture flow rate, if necessary, to achieve a suitable degree of particle capture.

Once the magnetic particle isolate is captured, a dispersion medium is introduced into capture zone 40 and the magnetic particle isolate is perfused with the dispersion medium. After perfusion, the dispersion medium is pulsed through capture zone 40 at a predetermined rate (referred to herein as a "dispersion rate") effective to dislodge the magnetic particle isolate from the capture zone, move the magnetic particles from the magnetic field, and suspend the magnetic particles in the dispersion medium to provide a second mixture. At the predetermined dispersion flow rate, the higher rate of flow through the fluid flow path permits viscous forces of the fluid to remove the captured particles from the capture zone. An inventive system in certain embodiments is capable of nondestructively separating even fragile particles, such as, for example, intact blood cells, from a carrier fluid. It is to be understood that the pulse can, in various embodiments, move the magnetic particles from the capture zone in either direction.

For example, in a system in which the fluid flow path has a diameter of about 0.02 inches, as described in detail below, a preferred pulse flow rate is from about 250 to about 2500 mm/s (200 µl/s=1018 mm/s in the system described; 500 uL/s=2500 mm/s, 50 uL/s=250 mm/s). More preferably, the pulse rate in a flow path of this diameter is from about 750 to about 1250 mm/s. A person of ordinary skill in the art will readily recognize that the preferred rate may vary depending upon other features of a given system, and will be able to make adjustments to the dispersion rate to achieve a suitable degree of particle dispersion.

Where it is desired to also separate the magnetic particles from the dispersion medium, the second mixture is then passed through the capture zone at a predetermined capture rate to again trap a major portion of the magnetic particles in the capture zone and thereby removed from the first dispersion medium to form a second magnetic particle isolate. It is readily understood that in a flow path having only one capture zone, passing the second mixture through the capture zone will require a reversal of the direction of fluid flow in the fluid flow path. This fluid flow reversal is effected by flow controller 50 imposing a reverse pressure on the mixture to cause the fluid to flow through the flow path in the opposite direction at a predetermined rate.

By controlling fluid flow rates through a fixed magnetic field in capture zone 40, as described above, the present invention provides systems that differ from prior art separation/resuspension by eliminating the need for removal of the magnetic field such as by physical movement of a permanent magnet away from the flow path or, where an electromagnet is used, by turning off the electromagnet or effecting field fluctuations or reversals. Furthermore, due to precisely controlled fluid flow in an inventive system, precise results can be obtained quickly using remarkably small amounts of reagents, samples, selective surfaces and the like. In certain preferred embodiments, the fluid flow path in the capture zone is essentially uninterrupted by scaffolds, rods or other magnetizable matrix structures and the particles are simply captured against the side of the flow path conduit. In other preferred embodiments, ferromagnetic structures are positioned within the flow path to produce high field gradients. Such structures are often useful, for example, for capturing nanoparticles.

The composition of carrier fluid and magnetic particles can vary depending on the particulars of the procedure being conducted. For instance, many commercial ELISA test kits are available that include magnetic particles with selective chemistry (immobilized antibodies), along with other reagents for use in a given assay. Thus, in one embodiment, the carrier fluid and magnetic particles include ELISA assay materials. As one representative example, a TNT RaPID Assay™ kit is available from Strategic Diagnostics (Newark, Del.) that includes TNT-horseradish peroxidase (TNT-HRP), a color development solution (3,3'5,5'-tetramethylbenzidine and $H_2O_2$), and a suspension of irregular 0.5 µm diameter magnetic particles with immobilized anti-TNT antibody. As another example, particles can be obtained that are covalently linked to specific oligonucleotide capture probes. Such particles can be utilized for selective purification of nucleic acid fragments from a biological sample. The term "nucleic acid" is used herein to refer to DNA nucleotides and RNA nucleotides, as well as any length polymer comprising DNA nucleotides or RNA nucleotides.

While the carrier medium described above can be an inert medium selected solely for transport of magnetic particles to the capture zone, in certain embodiments of the invention, the carrier medium includes a test sample, i.e., a sample in which the presence and/or the quantity of a specific analyte is to be determined. As such, initial contact of the particles and the carrier medium begin an incubation period that ends only when the magnetic particles are separated from the carrier medium as described above. Of course, in certain assays, such as, for example, a competitive immunoassay, the carrier medium may also include one or more additional reagents.

It is readily understood by a person of ordinary skill in the art that, in order to provide acceptable results, many chemical and biological assays require one or more wash steps in which unreacted reagents and/or target substances that are not bound to the magnetic particles are washed from the particles. As such, the dispersion medium in the procedure described above can be a wash solution. It is also readily understood that it is often desirable to conduct multiple wash steps to improve the accuracy of the test or assay. As such, in certain embodiments of the invention, resuspension and recapture of the magnetic particles can be preformed a plurality of times generally as described above.

Many such tests or assays also require suspension of the isolate in a specific reagent (referred to herein as an "analysis reagent"). For example, in certain enzyme-bound immunoassay procedures, isolated substances are contacted with or suspended in a substance that produces color when acted upon by the bound enzyme. As such, certain inventive methods include perfusing a magnetic particle isolate with a dispersion medium including an analysis reagent, pulsing the medium through the capture zone to dislodge the magnetic particle isolate from the capture zone, move the magnetic particles from the magnetic field, and suspend the magnet particles in the analysis reagent-containing medium. After the suspension is allowed to incubate for a predetermined period of time, this suspension is then passed through the capture zone to once again capture magnetic particles from the suspension, so that one or more physical and/or chemical properties of the medium containing the analysis reagent, or the magnetic particle isolate itself, can be measured.

Figure 2:
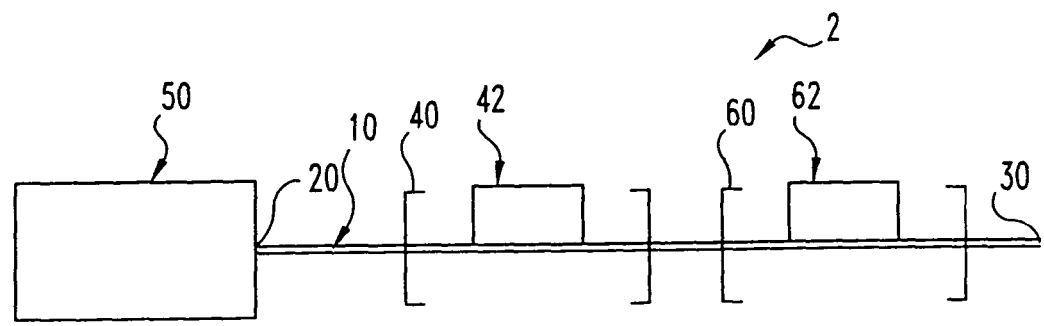
FIG. 2 is a schematic view of a second embodiment of a system in accordance with the invention.

Referring now to FIG. 2, fluid flow system 2 is shown that includes a detection zone 60 and detector 62. Detector 62 is in fluid communication with, or makes up a portion of, the fluid flow path, and is positioned to detect a physical or chemical property of a fluid in the detection zone. The detection zone 60 may be separate from the capture zone 40 (as depicted schematically in FIG. 2), or the detection and capture zones may partially or completely overlap. The present invention contemplates that a wide variety of detectors can be used in various applications of the invention, including but not limited to optical detectors, pH detectors, radiation detectors, viscosity detectors and the like.

The type of detector used in accordance with the invention can vary depending upon the particular type of analysis being performed, and it is well within the purview of a person of ordinary skill in the art to select and configure a suitable detector for use in accordance with the invention. For example, a variety of assays depend upon the development of color in an analysis reagent for the identification and quantification of an analyte. For such assays, the detector can be a spectrophotometer or other optical detector configured to pass light or other electromagnetic radiation of a given wavelength through the solution to measure the degree of color development. As one example, the detector described in greater detail below includes a U-shaped transmittance flow cell machined from FEP (McMaster-Carr, Los Angeles, Calif.) and used for absorbance measurements downstream from trapped magnetic particles. The optical path is 1 cm long and absorbance measurements were made using an Ocean Optics (Dunedin, Fla.) fiber optic spectrophotometer and tungsten halogen lamp. A 400 µm quartz fiber was used for detection. An embodiment including a permanent magnet and an optical detector as described is set forth in FIG. 8.

For assays in which added sensitivity is required, one may wish to modify the assay to utilize other detection schemes such as chemiluminescence or liposome-based immunoassays which increase sensitivity by several orders of magnitude. A wide range of labels (i.e., radioactive isotopes, chromogenic or luminescent groups, etc.) can be used and a person of ordinary skill in the art can select and implement a suitable detector for a wide variety of such assays.

Figure 3:
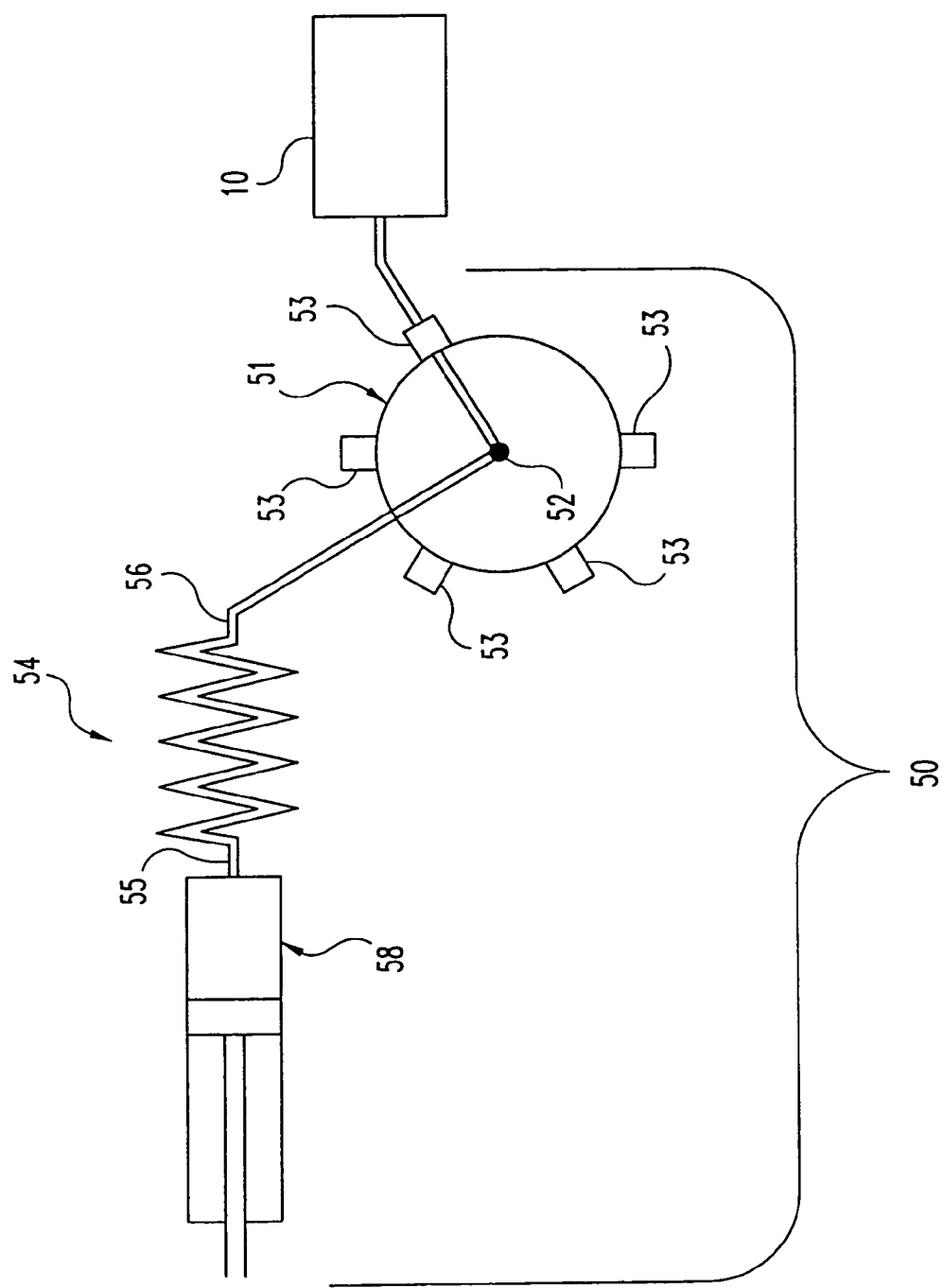
FIG. 3 is a schematic view of an embodiment of a flow controller in accordance with the invention.

Fluid flow controller 50 can have a wide variety of configurations in accordance with the invention. In one embodiment, depicted in FIG. 3, flow controller 50 comprises a multi-port selection valve 51, a holding coil 54 and a variable speed reversible pump. In this embodiment, multi-port selection valve 51 includes a primary port 52 and a plurality of secondary ports 53. One of the secondary ports is fluidly connected to the fluid flow path 10, and primary port 52 is fluidly connected to holding coil 54. The other secondary ports 53 are optionally fluidly connected respectively to sources of various fluids to be used in a given separation/resuspension procedure. Still other ports can be used for drawing air into the holding coil or for dispelling waste from the system, as discussed in greater detail below. Proximal end 55 of holding coil 54 is fluidly connected to variable speed reversible pump 58. In one embodiment, pump 58 is a syringe pump including a stepper-motor, which pumps are well known in the pertinent field. It is of course not intended that the invention be limited to this type of pump, it being understood that alternative pump designs can be used as would occur to a person of ordinary skill in the art. Holding coil 54 is used as a reservoir for holding a sample, extraction material or reagents. In each step of a sequential injection procedure, a liquid or slurry is aspirated into the holding coil via a selected valve port, then the valve is switched to the flow path port and the coil contents are injected into the flow path. Air separators prevent bead slurry, sample, and other solutions from mixing or dispersing in the holding coil.

Figure 4:
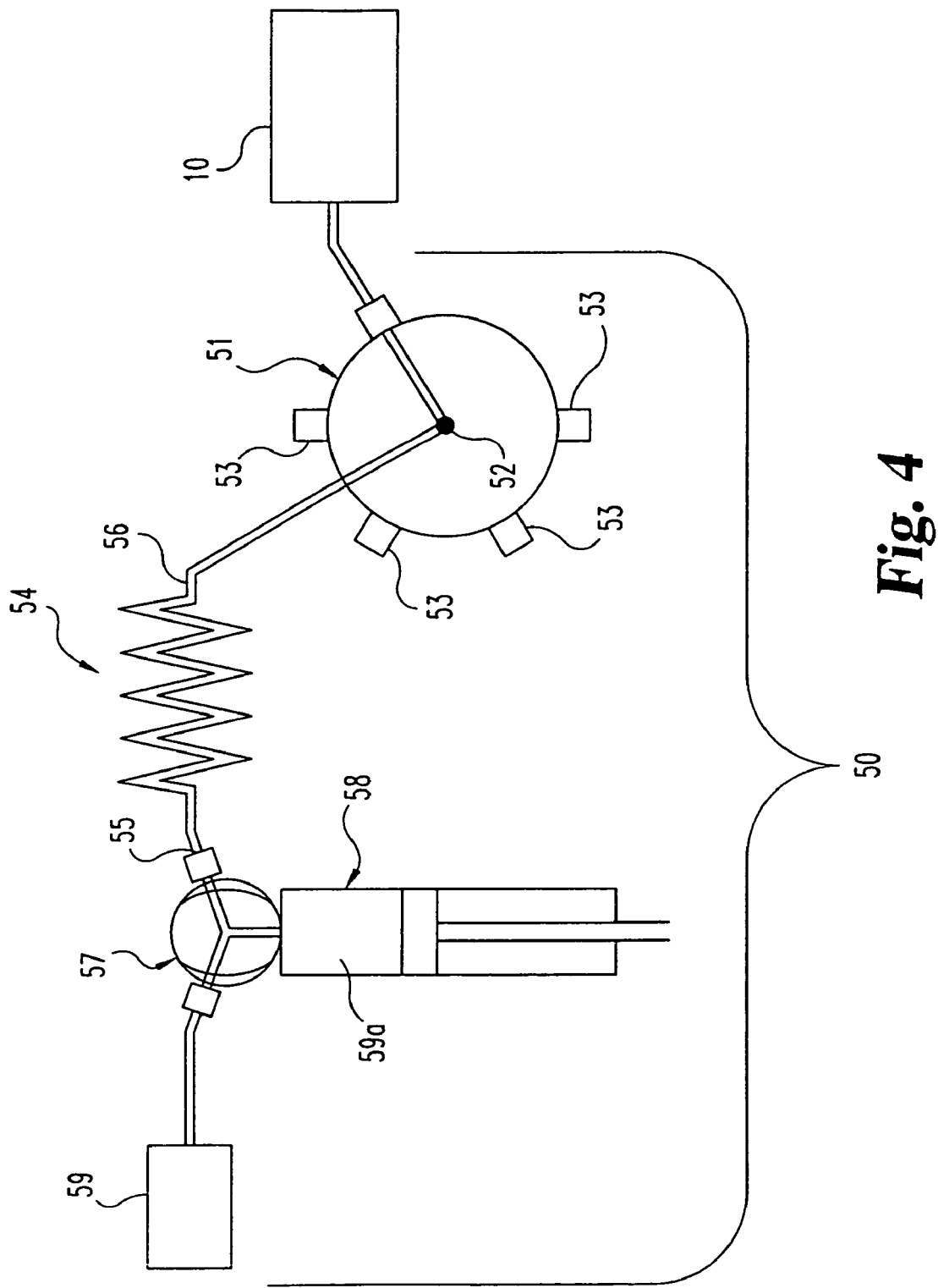
FIG. 4 is a schematic view of another embodiment of a flow controller in accordance with the invention.
Figure 5:
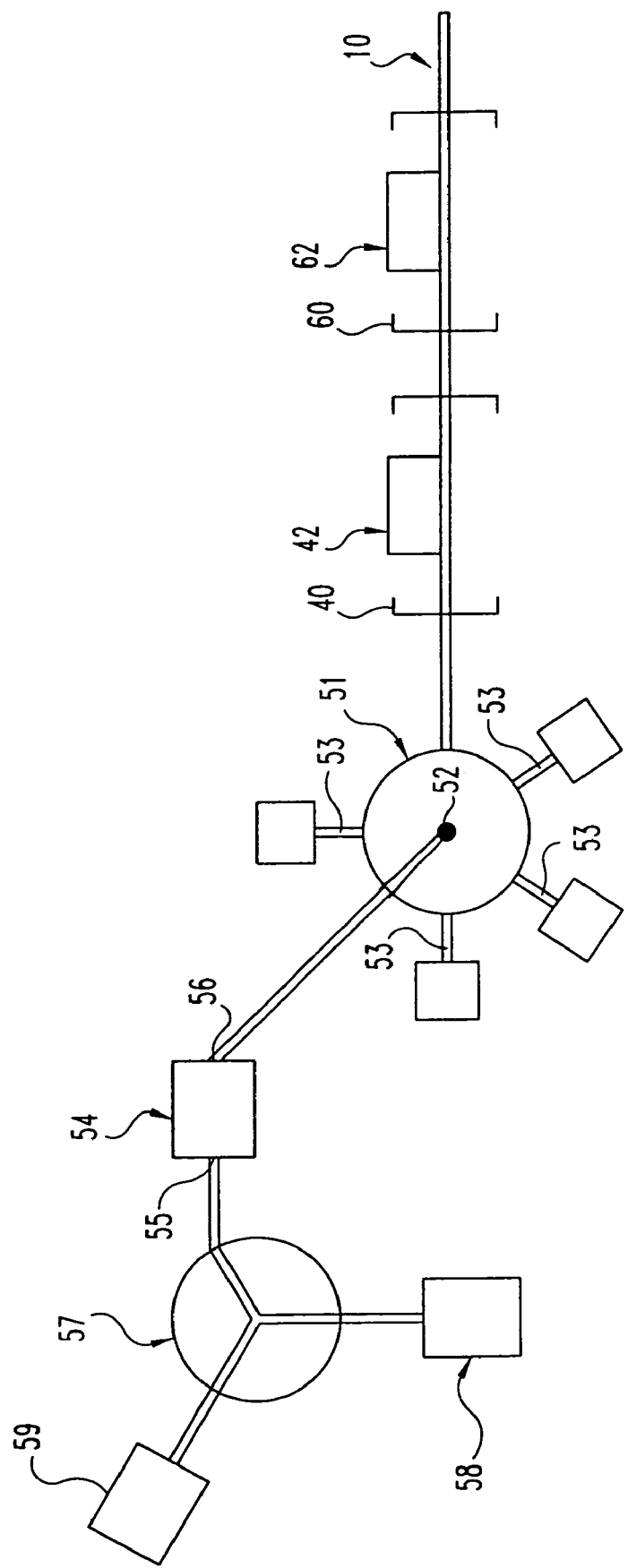
FIG. 5 is a schematic view of a third embodiment of a system in accordance with the invention.
Figure 6:
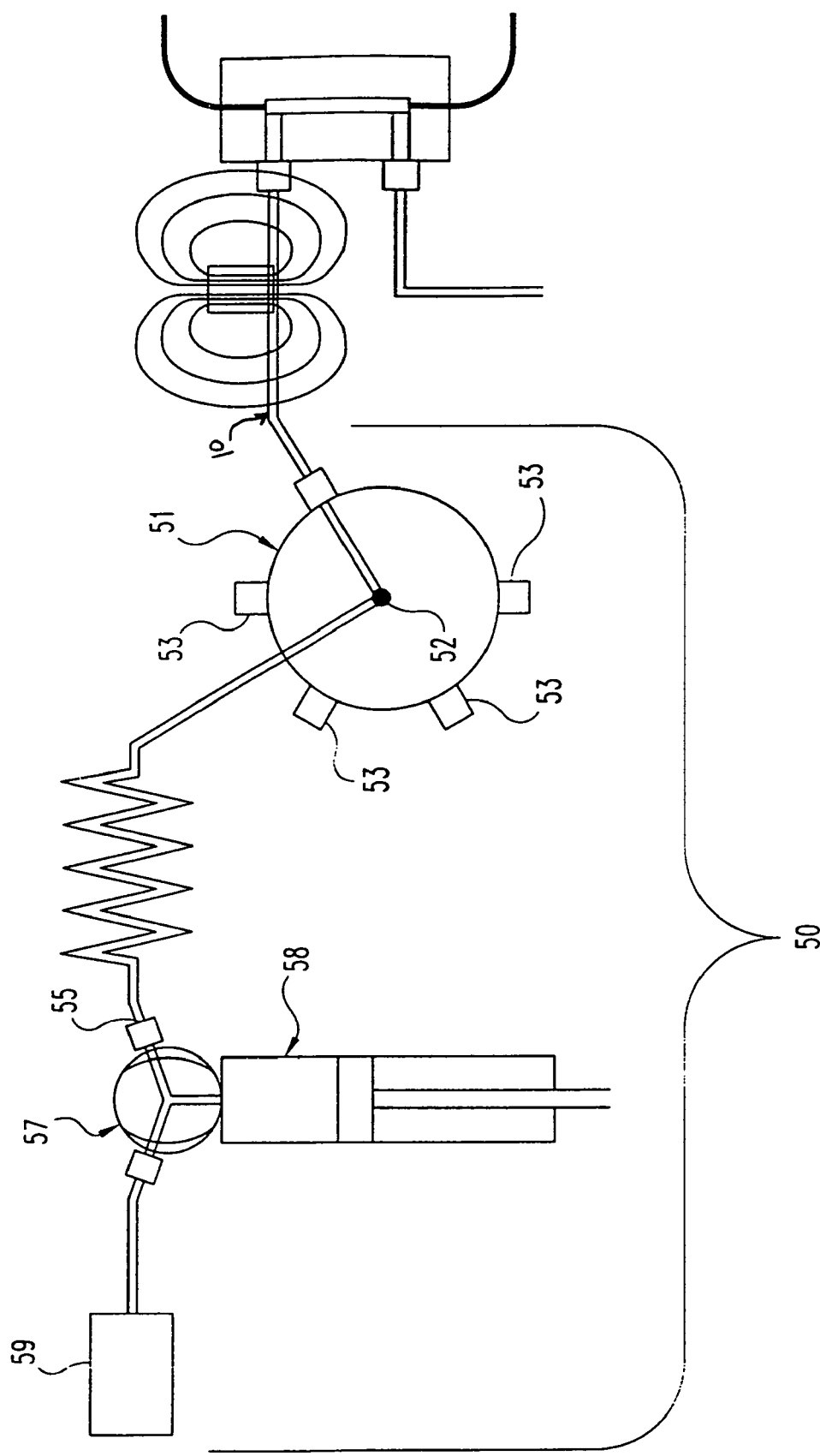
FIG. 6 is a schematic view of a fourth embodiment of a system in accordance with the invention.

In another embodiment, depicted in FIGS. 4-6, flow controller 50 also includes a multiport valve 57 positioned between and fluidly connected to the holding coil and the variable speed reversible pump. In this embodiment, proximal end 55 of holding coil 54 is connected to a first port of the valve, and a second port of the valve is fluidly connected to the variable speed reversible pump. A third port of the valve can conveniently be connected to a source 59 of a wash solution or other reagent for use in flushing and/or cleaning the fluid flow path upon completion of a given assay. Thus, in this embodiment, after a given series of separations/resuspensions, valve 57 switches to fluidly connect pump 58 and source 59, and pump 58 draws fluid from source 59 into reservoir 59a. After a desired volume of fluid is drawn, valve 57 switches again to fluidly connect pump 58 and holding coil 54, and pump 58 propels the fluid through the holding coil, selection valve 51 and flow path 10 to thereby flush any remaining magnetic particles and/or reagents therefrom.

In one manner of performing a separation/resuspension procedure using this system, one of secondary ports 53 is fluidly connected to a source of magnetic particles in a carrier medium. Selection valve 51 is positioned to provide fluid communication between primary port 52 and the particle/medium mixture source, and pump 58 exerts a negative pressure, thereby drawing a quantity of the mixture into holding coil 54. Selection valve 51 then moves to provide fluid communication between holding coil 54 and fluid flow path 10. After a desired period of time of further incubation (if additional time is necessary in a given procedure), pump 58 exerts a positive pressure, thereby propelling the mixture through selection valve 51, into fluid flow cell 10 and through capture zone 40. The rate of flow through capture zone is sufficiently slow to allow a major portion of the magnetic particles in the mixture to be captured in capture zone 40 by force of the magnetic field, thereby providing a magnetic particle isolate.

Where the magnetic particles are derivatized magnetic particles and the carrier medium includes a sample to be tested for the presence and/or quantity of a particular analyte, it is understood that the particles must remain in contact with the medium for a carefully controlled period of time to provide acceptable assay results. Therefore, in a procedure in which contact between the particles and the sample is to be maintained for a specified length of time, it is important to initiate a timing sequence from the time of initial contact thereof.

In an automated system, the carrier medium is an inert carrier, and the magnetic particles remain separated from the test sample until mixing occurs in the holding coil or in the fluid flow cell. In this embodiment, a test sample and other reagents, if needed, are placed, separately or in a premixed solution, in fluid communication with one or more of the other secondary ports 53.

Where mixing of the magnetic particles and test sample is to occur in the holding coil, magnetic particle suspension, test sample and other reagents, separately or in some premixed combination, are alternately drawn into holding coil by coordinated movement of selection valve 51 and pump 58. As quantities of each are alternately drawn into holding coil (to form a "stacked zone"), the quantities become intermixed, thereby initiating an incubation period during "stacking" of the holding coil. After the particles/sample/reagents are stacked in the holding coil (without air separation in this case), and optionally after a desired period of time of further incubation (if additional time is necessary in a given analysis), selection valve 51 moves to provide fluid communication between holding coil 54 and flow path 10, and pump exerts a reverse pressure on the fluids to move the fluids through selection valve 51, into flow path 10, and through capture zone at a predetermined capture rate as described above, for separation of the magnetic particles from the other fluids.

Where mixing is to occur in the flow cell, a magnetic particle suspension in an inert carrier is first drawn into holding coil by coordinated movement of selection valve 51 and pump 58, and aspirated first into the flow path and through capture zone at a predetermined capture rate to provide a magnetic particle isolate wherein the selective surfaces of the particles are as yet unreacted. Subsequently, test sample and other reagents, separately or in some premixed combination, are passed into flow path 10 to perfuse the isolate and resuspend the particles. Where a specific order of contact is desired for a given analysis, it is of course understood that the order in which fluids are aspirated into flow path 10 is readily controlled by the coordinated control of selection valve 51 and pump 58. Furthermore, if additional mixing of fluids is desired as an intermediate step of an inventive procedure, it is understood that a resuspended magnetic particle mixture or other fluids can be mixed in holding coil by creating a "stacked zone" in holding coil 54 by coordinated control of selection valve 51 and pump 58 generally as described above.

Once a magnetic particle isolate is formed by separation of magnetic particles from the carrier medium, the magnetic particle isolate is perfused with a dispersion medium, such as, for example, a wash solution. In certain embodiments, dispersion medium is already present in reservoir 59a or present in holding coil 54 "behind" the mixture. In other embodiments, such as that depicted in FIG. 4, a source of dispersion medium can be accessed by movement of valve 57 to provide fluid communication between pump 58 and source 59, aspiration of dispersion medium into reservoir 59a, movement of valve 57 to provide fluid communication between pump 58 and holding coil 54, and reversal of pressure applied by pump 58 to cause dispersion medium to flow through coil 54, through selection valve 51 and into flow path 10. In such embodiments, dispersion medium can be aspirated and dispensed into flow cell 10 without further movement of selection valve 51. In other embodiments, a dispersion medium source is accessible through one of secondary ports 53 of selection valve 51. In such an embodiment, dispersion medium is aspirated into flow cell 10 by first drawing dispersion medium into holding coil 54. In such an embodiment fluid communication between holding coil 54 and dispersion medium source is provided by movement of selection valve 51, pump 58 exerts a negative pressure, thereby drawing a quantity of the dispersion medium into holding coil 54. Selection valve 51 then moves to again provide fluid communication between holding coil 54 and fluid flow path 10, and pump 58 exerts a positive pressure, thereby propelling the medium through selection valve 51, into fluid flow cell 10 and through capture zone 40. The rate of flow through the capture zone is initially sufficiently slow to prevent disruption of the magnetic particle isolate. After some of the dispersion medium perfuses the isolate, pump 58 exerts a greater pressure (positive or negative) for a brief period of time to cause a fluid flow pulse in the capture zone having a flow rate high enough to dislodge the magnetic particle isolate from the capture zone, move the magnetic particles from the magnetic field, and suspend the magnetic particles in the dispersion medium to provide a second mixture.

The magnetic particles can be separated from the dispersion generally as described above and again resuspended and reseparated one or more times in the same or different media. Alternatively, the second mixture can be passed to detection zone 60 for detection of one or more physical or chemical features, or can be collected for further processing of another type.

Figure 7:
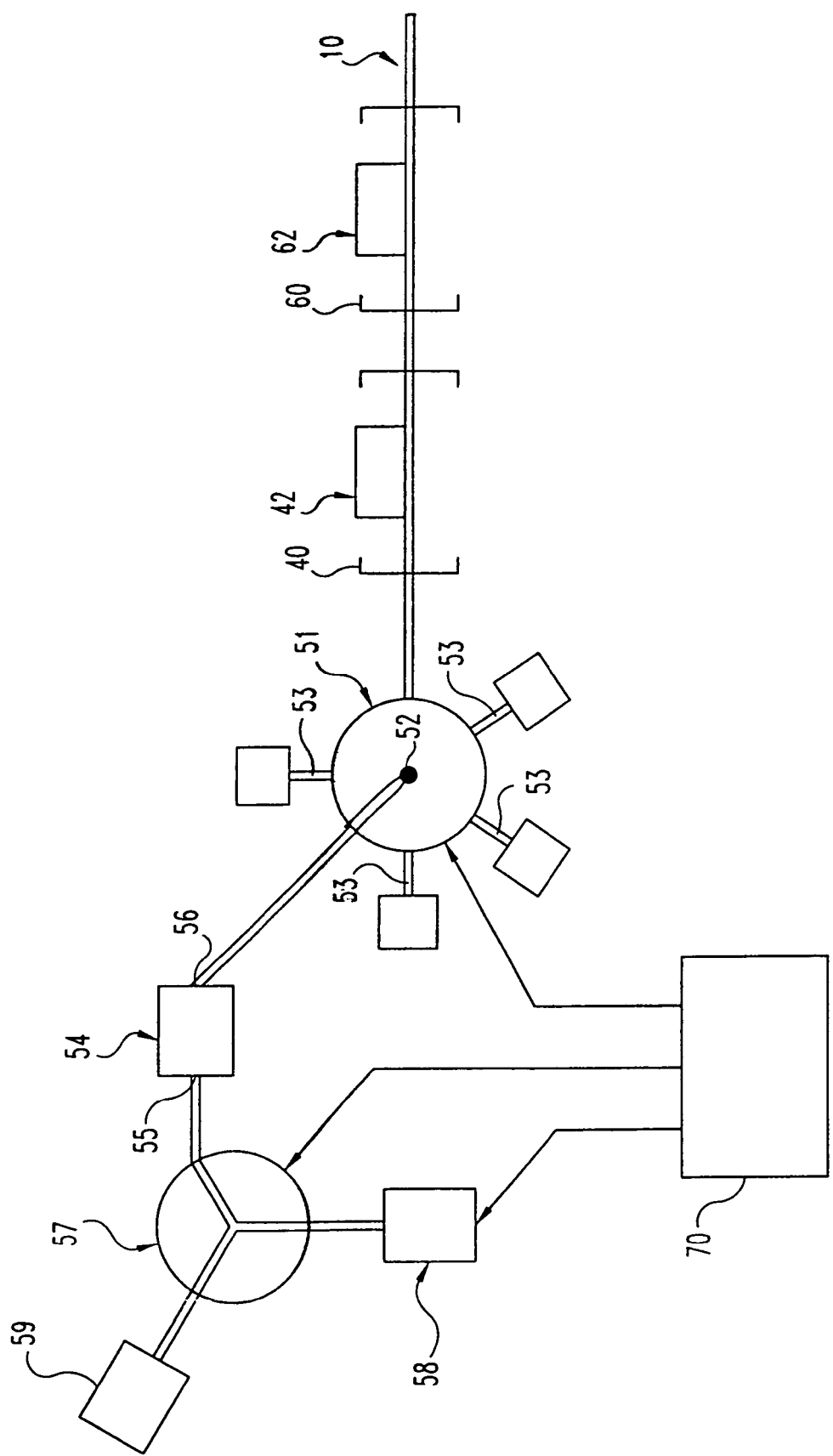
FIG. 7 is a schematic view of a fifth embodiment of a system in accordance with the invention.

In particularly preferred embodiments of the invention, selection valve 51, pump 58 and valve 57 (where present) are under the control of a pre-programmed sequencer 70 as depicted schematically in FIG. 7. Sequencer 70 controls the movement of valves to provide fluid communication between desired flow cells and controls the pump to provide positive or negative pressure of desired magnitudes at appropriate times, examples of which are discussed above, thereby coordinating the movement of fluids through fluid flow path 10. In further embodiments, such as, for example, where sequencer 70 is a computer, the computer may also be configured to receive information from detector 62 and analyze, tabulate, interpret and/or display such information.

Sequencer 70 may be comprised of one or more components configured as a single unit. Alternatively, when of a multi-component form, sequencer 70 may have one or more components remotely located relative to the others, or otherwise have its components distributed throughout the system. Sequencer 70 may be programmable, a state logic machine or other type of dedicated hardware, or a hybrid combination of programmable and dedicated hardware. One or more components of sequencer 70 may be of the electronic variety defining digital circuitry, analog circuitry, or both. As an addition or alternative to electronic circuitry, sequencer 70 may include one or more mechanical, hydraulic, pneumatic, or optical control elements.

In one embodiment including electronic circuitry, sequencer 70 is based on a solid state, integrated microprocessor or microcontroller with access to one or more solid-state memory devices (not shown). It is preferred that this memory contain programming instructions to be executed by the microprocessor or microcontroller, and be arranged for reading and writing of data in accordance with one or more routines executed by sequencer 70. In further embodiments, sequencer 70 is an industrial grade ruggedized programmable personal computer with customized software and hardware to practice the present invention. This preferred configuration can include communication interfaces such as modem or network links, and subsystems to accommodate removable media, such as compact disks (CDs) or floppy disks. Although it is preferred that the processor be readily reprogrammable by software, it may also be programmed by firmware, or be configured as an integrated state machine, or employ a combination of these techniques. In yet a further form, sequencer 70 is provided with one or more programmable logic control (PLC) units.

Any memory associated with sequencer 70 may include one or more types of solid-state electronic memory and additionally or alternatively may include the magnetic or optical variety. For example, the memory may include solid-state electronic Random Access Memory (RAM), Sequentially Accessible Memory (SAM) (such as the First-In, First-Out (FIFO) variety or the Last-In First-Out (LIFO) variety), Programmable Read Only Memory (PROM), Electrically Programmable Read Only Memory (EPROM), or Electrically Eraseable Programmable Read Only Memory (EEPROM); an optical disc memory (such as a CD ROM); a magnetically encoded hard disc, floppy disc, tape, or cartridge media; or a combination of any of these types. Also, the memory may be volatile, nonvolitile or a hybrid combination of volatile and nonvolatile varieties.

Sequencer 70 can also include any control clocks, interfaces, signal conditioners, filters, limiters, Analog-to-Digital (A/D) converters, Digital-to-Analog (D/A) converters, communication ports, or other types of operators as would occur to those skilled in the art to implement the present invention.

Use of a flow controller as described above for sequential injection offers several advantages for immunoassays. The highly reproducible timing obtained with sequential injection allows for accurate analysis that can extend into non-equilibrium measurements, if desired, in a very short time frame not generally considered or achieved by a manual technique. Sample volumes injected can be very small, and there is also very low reagent consumption.

As stated above, the fixed magnetic field that intercepts capture zone 40 can be provided by a permanent magnet having a fixed relationship to flow path 10 or by an electromagnet having a fixed relationship to flow path 10 and generating a substantially constant field strength. One advantage of permanent magnets is that they do not generate heat during operation, which could interfere with the analysis. Where the magnetic field is provided by a permanent magnet, the magnet can have a wide variety of configurations, including configurations commonly referred to as a horseshoe configuration or a standard bar configuration. For example, the permanent magnet or magnets can have a rectangular cross-section and in certain embodiments can be glued or fixed by mechanical means to the fluid flow path conduit or to a non-magnetic holding support to form a permanent magnet assembly. In further embodiments, the assembly can include a ferromagnetic harness to house the magnet or magnets and to intensify and focus the magnetic field. The magnets are preferably oriented with their magnetic lines of force perpendicular to the longitudinal axis of the flow path. Alternate cross-sectional shapes, orientations, and magnetic pole orientation with respect to the container are also envisioned.

In addition, permanent magnets can have a variety of compositions. Permanent magnets of rare earth alloys having a surface field strength in the range of several hundred Gauss to several kilo-Gauss are preferred. In one embodiment, the permanent magnet is a high energy permanent magnet made from Neodymium-Iron-Boron or Samarium-Cobalt. Such magnets, and a wide variety of alternative permanent magnets suitable for use in connection with the invention are available commercially. A wide variety of such configurations and compositions are included within the meaning of the term "permanent magnet" as used herein.

Figure 8:
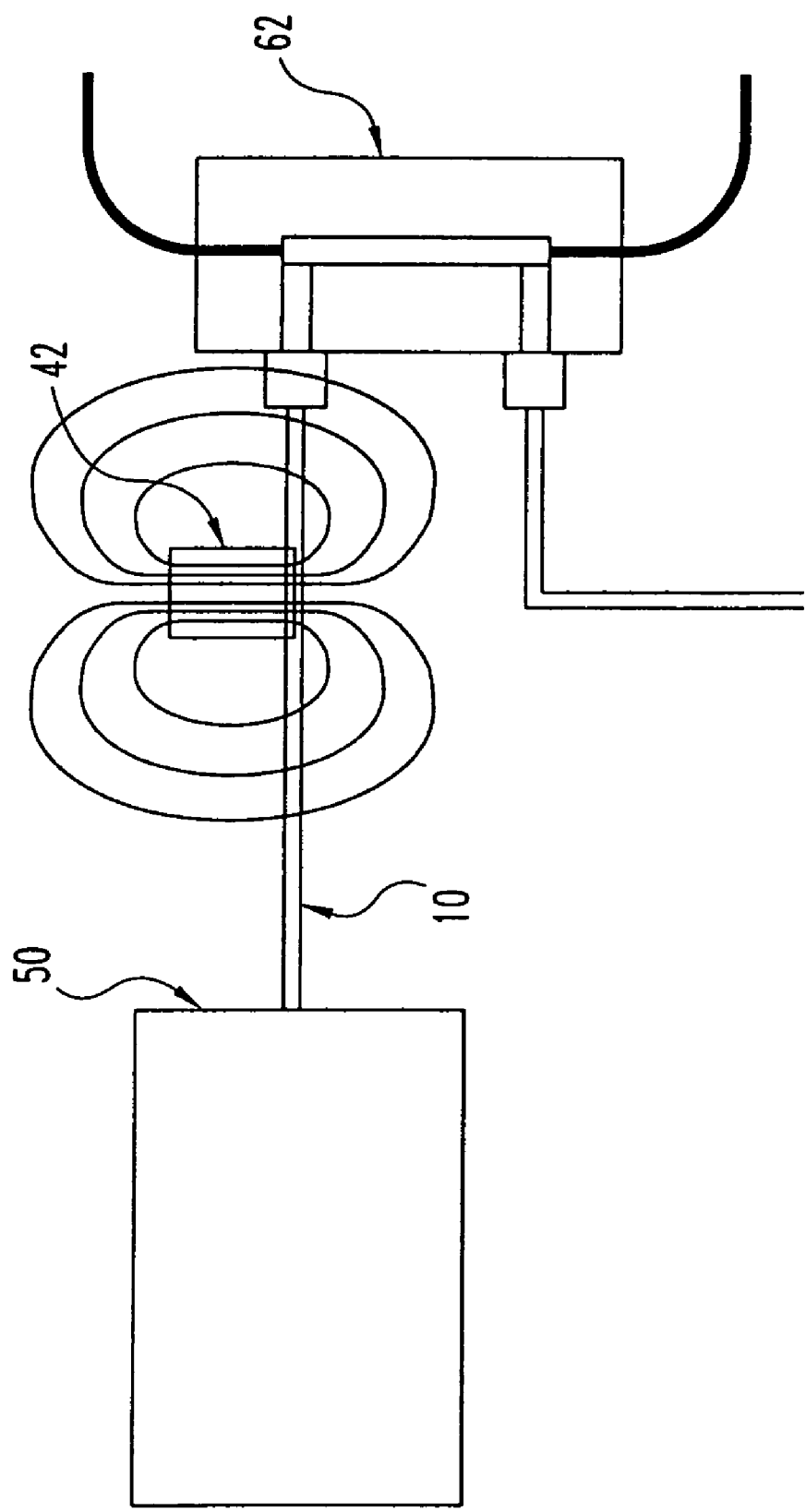
FIG. 8 is a schematic view of a sixth embodiment of a system in accordance with the invention.

In a standard bar magnet, gradients exist because the magnetic field lines follow non-linear paths and "fan out" or bulge as they move from North to South, as depicted schematically in FIGS. 6 and 8. These effects typically create gradients of about 0.1 to 1.5 kGauss/cm in high quality laboratory magnets. While it is not necessary to the invention, a person of ordinary skill in the art will recognize that these gradients can be increased by manipulating the magnetic circuits so as to compress or expand field line density. For example, if the gradient at one pole of a bar magnet is of insufficient strength, moving a second bar magnet with an identical field in opposition to the first magnet would cause repulsion between the two magnets. The number of field lines would remain the same, but they would become compressed as the two magnets were forced closer together. Thus, an increased gradient would result. The addition of magnets of opposing field to this dipole configuration to form a quadrupole could further increase the size of the region of high gradients. Other configurations such as adjacent magnets of opposing fields would also create gradients higher than those seen in a bar magnet of equivalent strength. Yet another method of increasing gradients in external field devices is by adapting the pole piece design. For example, if the configuration of a standard dipole magnet were changed by making one of the magnets into a pointed magnet, all field lines would flow towards the point, dramatically increasing the gradient around that region.

In accordance with the invention, the magnetic field in the capture zone of the fluid flow path has a strength that will capture magnetic particles selected for use in accordance with the invention at a relatively low flow rate (i.e., a flow rate of from about 1 to about 13 mm/s), and that is not great enough to retain the particles in a fluid flow having a relatively high flow rate (i.e., a flow rate of from about 250 to about 2500 mm/s). It is readily understood that the preferred field strength may vary depending upon a variety of factors, including, but not limited to, the inner dimensions of the flow cell in the capture zone and at other locations, the size and susceptibility of the magnetic particles used in a given procedure, and the desired rates of separation and perfusion if a given procedure calls for such. It is well within the purview of a person of ordinary skill in the art, in view of the present specification, to select a field strength and to select a suitable magnetic field source, whether of the permanent magnet or electromagnet variety, for a wide variety of inventive systems. In one preferred embodiment, the capture zone includes average magnetic field gradients of 0.1 to 2 kGauss/cm. In another preferred embodiment, ferromagnetic materials are placed within or in close proximity to the flow path to produce localized regions of high magnetic field gradient for capturing smaller, less magnetic particles.

Turning now to the magnetic particles themselves, the term "magnetic particle" is used herein to refer to a particle that is responsive to a magnetic field. Magnetic particles selected for use in accordance with the invention preferably include a ferromagnetic material, more preferably a superparamagnetic material. Superparamagnetic materials, regardless of their size (i.e., often ranging from 25 nm to 100 microns,) have the property that they are only magnetic when placed in a magnetic field. Once the field is removed, they cease to be magnetic and can normally be dispersed into suspension. The basis for superparamagnetic behavior is that such materials contain magnetic material in size units below 20-25 nm, which is estimated to be below the size of a magnetic domain. A magnetic domain is the smallest volume for a permanent magnetic dipole to exist. Hence, these materials are formed from one or more or an assembly of units incapable of holding a permanent magnetic dipole. Such magnetic particles are commonly of polymeric material containing a small amount of ferro-magnetic substance such as iron-based oxides, e.g., magnetite, transition metals, or rare earth elements, which causes them to be captured by a magnetic field. The magnetic material of choice is magnetite, although other transition element oxides and mixtures thereof can be used.

For many preferred applications of the invention, the surface of magnetic particles is coated with a ligand or receptor, such as antibodies, lectins, oligonucleotides, or other bioreactive molecules, which can selectively bind a target substance in a mixture with other substances. The surface chemistry of the magnetic particle can also be used to capture target substances due to electrostatic interactions, van der Waals interactions, dipole-dipole interactions or hydrogen bonding interactions between the target substances and the surfaces of the magnetic particles. Magnetic particles have been used for various applications, particularly in health care, e.g. immunoassay, cell separation and molecular biology, and many such particles are available commercially. Superparamagnetic particles useful for performing such procedures should provide for an adequate binding surface capacity for the adsorption or covalent coupling of one member of a specific affinity binding pair, i.e., ligand or receptor.

Some magnetic particles are composed of spherical polymeric materials into which has been deposited magnetic crystals. These materials, because of their magnetite content and size, are readily separated in relatively low fields (0.5 to 2 kGauss/cm) which can easily be generated with open field gradients. Another similar class of materials are particles that typically are produced in the size range of from about 0.5 to about 0.75 microns. Another class of suitable material includes particles that are basically clusters of magnetite crystals, about 1 micron in size, which are coated with amino polymer silane to which bioreceptors can be coupled. These highly magnetic materials are easily separated in relatively low gradients (i.e., gradients as low as 0.5 kGauss/cm) and, due to their size, they can remain suspended for extended periods of time.

The preferred diameter of a magnetic particle used in accordance with the invention is in the range between 0.1 to 300 microns. Magnetic particles are today widely available commercially, with or without functional groups capable of binding antibodies or DNA molecules or containing other binding sites for sample purification. Suitable paramagnetic particles are commercially available from Dynal Inc. of Lake Success, N.Y.; PerSeptive Diagnostics, Inc., of Cambridge, Mass.; and Cortex Biochem Inc., of San Leandro, Calif.

Another type of magnetic material that can be used in accordance with the invention are nanosized colloids (see, for example, U.S. Pat. No. 4,452,773 to Molday, U.S. Pat. No. 4,795,698 to Owen et al, U.S. Pat. No. 4,965,007 to Yudelson; and U.S. patent application Ser. No. 07/397,106 by Liberti, et al). Nanosized colloids are typically composed of single to multicrystal agglomerates of magnetite coated with polymeric material which render them aqueous compatible. Individual crystals can range in size from about 8 to about 15 nm. The coatings of these materials have sufficient interaction with aqueous solvent to keep them in the colloidal state almost, if not, permanently. A person of ordinary skill in the art will recognize that, because of their size and interaction with solvent water, substantial magnetic gradients are required to separate nanosized colloids. Therefore, in a system in which such colloids are used, magnetic fields of greater strength are preferred.

One advantageous feature of the invention is that the time during which magnetic particles are suspended in a given reagent or other medium can be precisely controlled. In addition, the inventive approach permits the implementation of an automated immunoassay that is quick and sensitive in the micromolar concentration range. A particularly advantageous use of the present invention is for the performance of an ELISA assay using an automated sequential injection procedure, which utilizes surface-derivatized magnetic particles to determine the amount of analyte in a test sample by competitive immunoassay.

Competitive immunoassays with magnetic-particle-bound antibodies and enzyme-amplified detection involve several steps. Using TNT as the analyte, for example, the first step is to mix the TNT sample, the TNT-enzyme conjugate, and immobilized antibodies. In a semi-automated procedure in accordance with the invention, these ingredients can be mixed, for example, in a polypropylene vial for competitive binding. The use of antibodies that are immobilized on magnetic particles facilitates separation of the solution components from the antibody-bound components in subsequent steps. Once the particles have been separated and washed, an analytical color development solution is added. This contains reagents for enzyme-catalyzed conversion of a substrate to a colored product for detection. After a precise reaction time, an absorbency measurement is made.

A typical sequence is as follows: (1) magnetic particles that are coated with antibodies against the analyte are mixed with the test sample including the analyte and an analyte-enzyme conjugate in which the enzyme acts upon a coloring reagent to produce color, and incubated for a predetermined period of time; (2) this mixture is aspirated into the fluid flow cell and through a capture zone in a fixed magnetic field, whereupon the magnetic field traps the particles in the flow path to form a magnetic particle isolate; (3) the magnetic particle isolate is resuspended in wash solution one or more times by aspiration and pulsing of a wash solution, with alternating recapture in the capture zone by a flow reversal and passage of the resuspended particles through the capture zone at a capture flow rate; (4) the washed magnetic particle isolate is resuspended in a coloring reagent by aspiration and pulsing of the reagent; (5) after a reaction period of a predetermined length, the magnetic particles are recaptured in the capture zone by a flow reversal and passage of the reagent and particles through the capture zone at a capture flow rate; (6) the coloring reagent is passed through an optical cell for detection of color development; and (7) a wash solution is passed through the flow cell at a relatively high rate to wash any remaining particles and/or reagents from the flow cell to condition the system for a subsequent procedure.

As such, in one embodiment, the present invention provides an automated ELISA instrument that requires minimal operator intervention. The automated ELISA system works like the manual procedure, but with smaller reagent volumes and shorter reaction times, and thus can be configured to provide a field-portable instrument capable of reliably and reproducibly analyzing test sample. The method is versatile and flexible and may therefore also be adapted to many different applications. The spent magnetic particles may be discharged after each analysis. This eliminates the problems of instability of reaction surfaces and eliminates the need for additional time traditionally required for regeneration of the solid-reacting phase in order to not only save time and increase sampling frequency but also to provide each individual sampling cycle with a fresh, uniform portion of magnetic particles. The spent magnetic particles are collected off line and may be regenerated later. The small volumes required, reduced sample handling, and precise reproducibility of inventive procedures have been shown to be useful for improving cumbersome, time-consuming, labor intensive, and semiquantitative traditional immunoassays.

In addition to the above-described embodiments, a variety of alternative configurations of the described systems are within the scope of the invention. As one example, the present invention contemplates a system in which the flow path includes multiple capture zones. In such an embodiment, a procedure could be performed in which fluid flow in the fluid flow path is unidirectional. In a system with multiple capture zones, magnetic particles can be separated from a carrier medium generally as described above in a first capture zone to provide a first magnetic particle isolate. The first isolate could then be resuspended by a pulse of a dispersion medium in the direction of a second capture zone to provide a second mixture. Flow could then be stopped if desired to provide a period of incubation between the capture zones, and then resumed in the same direction to pass the second mixture through the second capture zone to separate the magnetic particles from the dispersion medium and thereby form a second magnetic particle isolate. Further resuspension/recapture steps could then be performed, in further capture zones on the fluid flow path, or in the same capture zones by also utilizing fluid flow reversals. Such a system can be used, for example, when several capture/resuspension steps are necessary for a given assay or other procedure.

In another embodiment, multiple assays can be performed on the same test sample by including reagents for multiple assays in fluid connection with secondary ports 53 of multiport selection valve 51 and sequentially running different assays on quantities of the same sample. For example, it may be desired to perform one assay on a sample, and then perform a different analysis on the same sample. In this embodiment, after completion of an assay and flushing the system with a wash solution or other cleansing reagent, the system can be configured to automatically mix the test sample with magnetic particles having different selective groups bound thereto, and perhaps other reagents to sequentially perform another assay.

Additional modifications are envisioned that address specific requirements of certain assays. For example, it is understood that certain color-development solutions undergo photocatalysis when exposed to light. As such, in embodiments that utilize a color development reagent, conduits defining the fluid flow path and other fluid transport pathways through which a coloring reagent passes are made of an opaque material or covered with an opaque material, such as, for example, a layer of tape, to prevent exposure of the coloring reagent to light or other electromagnetic radiation. It is also understood that tape or other opaque material can also be used to cover flow lines that might contain or transport other light-sensitive reagents.

Similarly, it is understood that certain uses of the invention involve materials, including but not limited to DNA, protein and combinations thereof, that are temperature sensitive. As such, an inventive system can optionally include temperature control for sample handling of biomolecules. Temperature control is useful for optimizing binding and elution rates for DNA hybridization and elution, as well as for DNA amplification using polymerase chain reaction (PCR) or other enzyme amplification methods requiring thermal cycling. Elevated temperature can help to purify a sample by excluding interferents either during analyte extraction from a sample or during a subsequent wash step. It is well within the purview of a person of ordinary skill in the art to include temperature control elements in an inventive apparatus and to perform inventive procedures at predetermined, controlled temperatures.

The invention will be further described with reference to the following specific Examples. It will be understood that these Examples are also illustrative and not restrictive in nature.

EXAMPLES

Example One

Sequential Injection Analysis of TNT in Water Using an Enzyme-Linked Immunosorbent Assay An experiment was conducted to demonstrate capture and resuspension of magnetic particles in an inventive system as follows:

Chemicals: TNT RaPID Assay™ kits provided the ELISA reagents (Strategic Diagnostics, Newark, Del.). The reagents used were a TNT-horseradish peroxidase (TNT-HRP) conjugate, a color development solution (3,3'5,5'-tetramethylbenzidine and $H_2O_2$), and the suspension of irregular 0.5 μm diameter magnetic particles with immobilized anti-TNT antibody. The color development reagent solution contained the chromogenic substrate 3,3',5,5'-tetramethylbenzidine (TMB) and $H_2O_2$. Exact formulations are proprietary, but optimized reagent formulations have been published for similar atrazine ELISAs using HRP-atrazine conjugate and TMB. C. S. Hottenstein, F. M. Rubio, D. P. Herzog, J. R. Fleeker and T. S. Lawruk, "Determination of trace atrazine levels in water by a sensitive magnetic particle-based enzyme immunoassay", *J. Agric. Food Chem.*, 44(11), (1996) 3576-3581.

Wash solution consisted of pH 6.2 0.033 M phosphate, 0.033 M NaCl, and 0.1% Polysorbate 20 (P20) (BiaCore, Piscataway, N.J.) non-ionic surfactant. Wash solution also served as carrier solution in the flow system. DNA Zap™ solutions were from Ambion (Austin, Tex.). A standard solution of TNT from Supelco of 1000 micrograms/ml TNT in acetonitrile was diluted to prepare TNT standards in pH 6.2 0.033 M phosphate, 0.033 M NaCl and 0.007% P20.

Apparatus: The flow system set forth in FIG. 9 was used, in which a FiaLab 3000 system (FIAlab Instruments, Inc., Bellevue, Wash.) provided the stepper-motor-driven syringe pump with a built-in 3-way valve (Cavro, Sunnyvalve, Calif.) and a 10-port Cheminert® selection valve (Valco, Houston, Tex.). The wash inlet, color inlet, and waste outlet were 0.030 inch i.d. fluorinated ethylene-propylene (FEP) tubing (Valco). The color inlet was shielded from light by shrink wrap tubing. The holding coil and cell outlet were also shielded from light. The 600 μl holding coil was 0.030 inch i.d. polyetheretherketone (PEEK) from Upchurch Scientific (Oak Harbor, Wash.). The flow line contacting the magnet, extending from the valve to the optical cell was 0.02 inch i.d. PEEK. The volume from the valve to the center of the magnetic zone was 22 μl, and from the center of the magnet to the optical cell was 18 μl.

A ½×¼×⅝ inch NbFeB permanent magnet was obtained from Dexter Magnetic Technologies (Windsor Locks, Conn.). The ¼×⅝ inch faces of the magnet were its poles. One pole was placed against the magnetic zone tubing, with the tubing running along the ⅝ inch length. The tubing had been thinned to create a flat surface for the magnet by filing one side of the 0.062 inch outside diameter 0.02 inch inside diameter PEEK tube until the total thickness was 0.045 inch.

In principle, this leaves 0.004 inch of tubing wall between the channel and the magnet; however the actual distance may have been somewhat larger or smaller due to variations in the centering of the channel in the tubing.

Figure 9:
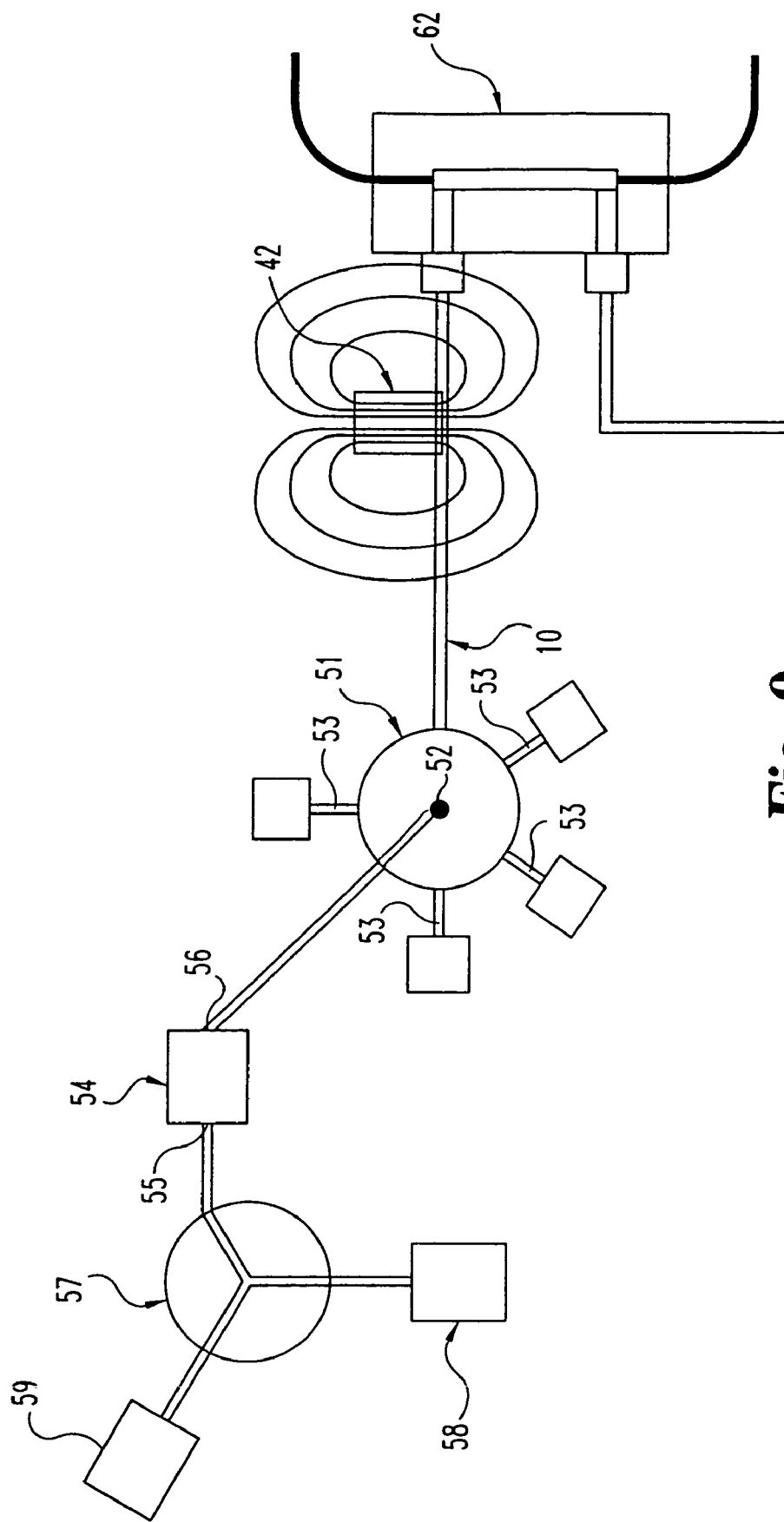
FIG. 9 is a schematic view of a seventh embodiment of a system in accordance with the invention.

A transmittance cell detector was drilled out of FEP (McMaster-Carr, Los Angeles, Calif.). As shown in FIG. 9, the inlet, outlet, and optical path of the detector formed a U-shaped channel. The inlet and outlet were tapped to accommodate Upchurch tube fittings. The flow channel through the optical path was 1 cm long and 1 mm in diameter. The illumination fiber was 400 μm and the collection fiber was 200 μm. Both fibers were quartz contained in 0.062 inch outside diameter stainless steel at the ends. Fiber ends were friction-fitted into the flow cell. The transparency of the FEP allowed the flow channel to be visible during method development. During actual runs, the cell was covered with tape to prevent photocatalysis of the color-development solution. The LS-1 tungsten halogen lamp and SD-2000 CCD array spectrometer were obtained from Ocean Optics (Dunedin, Fla.). A type NG5 optical filter (Schott Glass Technologies, Inc., Duryea, Pa.) was necessary to attenuate the lamp. With this filter, the integration time of the CCD was set at 75 milliseconds per scan to maintain a safe margin away from light saturation at 630 nm. Absorbency was monitored at $\lambda_{max}$ of the enzyme product, 630 nm, relative to the baseline monitored at 730 nm to correct for instrument variations and refractive index mixing in the optical path.

System software was written using VisualC++ (Microsoft, Redmond, Wash.) and the OOIWinIP dynamic link library (Ocean Optics) for controlling the CCD spectrometer.

Methodology, Semi-Automated Procedure:

Fluid and Magnetic Particle Handling. The competitive immunoassay on magnetic particles, with enzyme-catalyzed amplification, entailed several fluid and particle handling steps. These are described in sequence below for a semi-automated procedure in which the competitive assay is set up in a vial by addition of 100 μL of analyte-containing sample, 200 μL of a suspension of magnetic particles with surface-immobilized antibodies, and 100 μL of analyte-enzyme conjugate in that order.

The semi-automated approach to be described begins after the competitive assay mixture has been mixed in the test vial. The instrument times the incubation period so that manual timing is not necessary, and the tedious manual separations are replaced by automatic particle capture in a magnetic flow cell, with fluidic delivery of wash solutions and the subsequent color development solution. Color development reaction time is no longer dependent on manual timing and no stop solution need be used. Instead, the instrument automatically delivers the colored product to the detector after a precise time.

In the semiautomated procedure, initial manual steps were used to inject TNT solution, magnetic particle suspension, and enzyme conjugate, in that order, into a polypropylene vial followed by 10 seconds of mixing. After an incubation time of 4 minutes, the sequential injection methods described in Table 1 were executed, using the sequential injection system shown in FIG. 9. For purposes of clarity, standard implementation details were omitted, namely the use of 10 μL air separators between fluids, and loading of fluids into the holding coil prior to each injection. At least 0.5 seconds of delay are scheduled after each syringe move to allow for pressure equilibration before switching the selection valve. This helps to maintain the air segments at atmospheric pressure. The carrier solution in the flow system was identical to wash solution. A small air segment is preferably used to isolate reagents from carrier solution in the flow controller, however, care is taken not to perfuse the final portion of a reagent and air separator through the flow path because air bubbles interfere with optical detection.

Programmed steps were used to pull the competitive assay mixture into the system, capture the magnetic particles having a mixture of TNT and enzyme conjugate bound to the anti-TNT antibodies, wash the particles, mix the particles with reagents for enzyme-catalyzed generation of a colored product, hold the particles for a precise color development time, recapture the particles, and deliver the colored solution through a transmittance cell for absorbency measurement. The peak area of the absorbency measurement was used for quantification. Table 1 describes the standard reference semi-automated procedure in greater detail. The color development time in this procedure was 4 minutes. The total time for one run was 17.2 minutes, from the beginning of the mixture incubation time to the completion of the absorbency measurement, discarding the particles, and clearing the mix and color inlets with air. This compares to an assay time of over 40 minutes for the manual procedure.

TABLE 1

Sequential Injection ELISA Procedure.

| | Procedural Step | Solution | Port | Volume, µl | Flow Rate, µl/s |
|---|---|---|---|---|---|
| 1 | Initialize mix inlet | beads, enzyme, sample | mix | | |
| 2 | Aspirate mix into the holding coil | beads, enzyme, sample | mix | 325 | 40 |
| 3 | Inject mix to the cell and capture beads | beads, enzyme, sample | cell | −320 | 2.5 |
| 4 | Disperse beads in 5 µl | beads suspended in enzyme + sample | cell | 5 | 200 |
| 5 | Discard residual mix and air segment in the holding coil into the mixture inlet | Wash, air separator | mix | −100 | 200 |
| 6 | Disperse beads in 15 µl | Beads suspended in enzyme + sample | cell | 15 | 200 |
| 7 | Capture and wash the beads wash | Wash | cell | −115 | 2.5 |
| 8 | Disperse beads in 15 µl of wash solution | Beads suspended in wash | cell | 15 | 200 |
| 9 | Capture and wash the beads | Wash solution | cell | −115 | 2.5 |
| 10 | Disperse beads in 5 µl | Beads suspended in wash | cell | 5 | 200 |
| 11 | Initialize color inlet | | | | |
| 12 | Aspirate into the holding coil | Color reagent | color | 200 | 40 |
| 13 | Inject color reagent while capturing beads | Color reagent | cell | −80 | 2.5 |
| 14 | Disperse beads in 15 µl | Beads suspended in color reagent | cell | 15 | 200 |
| 15 | Incubate for colorTime minutes | | | | |
| 16 | Capture beads while inject color peak to the optical cell | Reacted color reagent | cell | −157 | 1 |
| 17 | Discard to waste through flow cell | Wash, air, color, beads | cell | −240 | 200 |
| 18 | Restore the color inlet | | | | |
| 19 | Restore the mix inlet | | | | |
| 20 | Rinse the holding coil | Wash | cell | −80 | 50 |

Initial conditions and inlet line preparation. The inlets at the beginning of an assay run were set up to contain 20 µL of wash solution extending out from the valve port (which helps to prevent unwanted pick up of air during valve switching) with the remainder of the tube containing air. To initialize a port before pulling solution into the holding coil, the volume of the tube (previously measured and a parameter in the program) plus 5 µL was pulled into the holding coil and then this volume plus an additional 30 µL of wash solution was expelled to waste. This fills the inlet tube with solution. After an assay, the mix and color ports were restored to the initial conditions.

Competitive mixture handling and magnetic particle capture. Before pulling in mix or color solution, a 10 microliter air segment was pulled into the holding coil. For the competitive mixture solution, 325 µL of the mixture was pulled into the holding coil at 40 µL/s using the 10 µl air segment to separate the mixture from the carrier solution. 320 µL of the sample were then pushed forward at 2.5 µL/s to capture magnetic particles on the tubing wall of the magnetic capture cell. The air segment and trailing wash solution were discarded out the mix port at 200 µL/s. Velocities less than 200 µL/s were not reliable for removing air from FEP tubing walls in 0.03 inch i.e. tubing. The presence of at least 0.007% of a surfactant such as P20 prevents breakup of air on hydrophobic surfaces.

Washing steps. Captured magnetic particles were washed by first resuspending them in solution using a 15 µL pulse at 200 µL/s that pulled the particles back toward the multiport valve. Thus, the particle suspension resided in the 22 µL zone between the valve and the magnetic capture zone. The particle suspension was then pushed back to the magnetic capture zone at 2.5 µL/s, capturing the particles and perfusing them with wash solution. The wash step pushed 115 µL of solution in the forward direction. There were two such wash steps in the standard procedure. The first of these steps completes pushing the competitive mixture solution through the magnetic cell followed by wash solution, while the second such step resuspends the particles in wash solution, recaptures, and perfuses them with wash solution.

Color development and detection. The particles were resuspended between the magnetic cell and the valve with a 5 µL pulse at 200 µL/s. The color port was initialized and an air segment was set up as described above; then 200 µL of color development reagent solution was pulled into the holding coil. 80 µL of color development reagent was pushed from the holding coil toward the flow cell at 2.5 µL/s to recapture the magnetic particles and perfuse them with solution. Then the particles were resuspended in reagent solution using a 15 µL pulse at 200 µL/s, again leaving the particles in the 22 µL zone between the valve and the magnetic capture zone. The particles resided here for the color development time, after which they were automatically recaptured in the magnetic cell while the solution was pushed through the transmittance optical cell at 1 µL/s. (The latter step used a 157 µL injection, using most of the color development reagent solution remaining to push the color peak through the optical cell.)

Wash and restoration steps. At the end of each semiautomated run, the inlet lines for the mix and color ports were cleared by pushing air out. Between runs, the inlets were set up to starting conditions as described above, and the holding coil was rinsed by expelling addition carrier (wash) solution.

Figure 10:
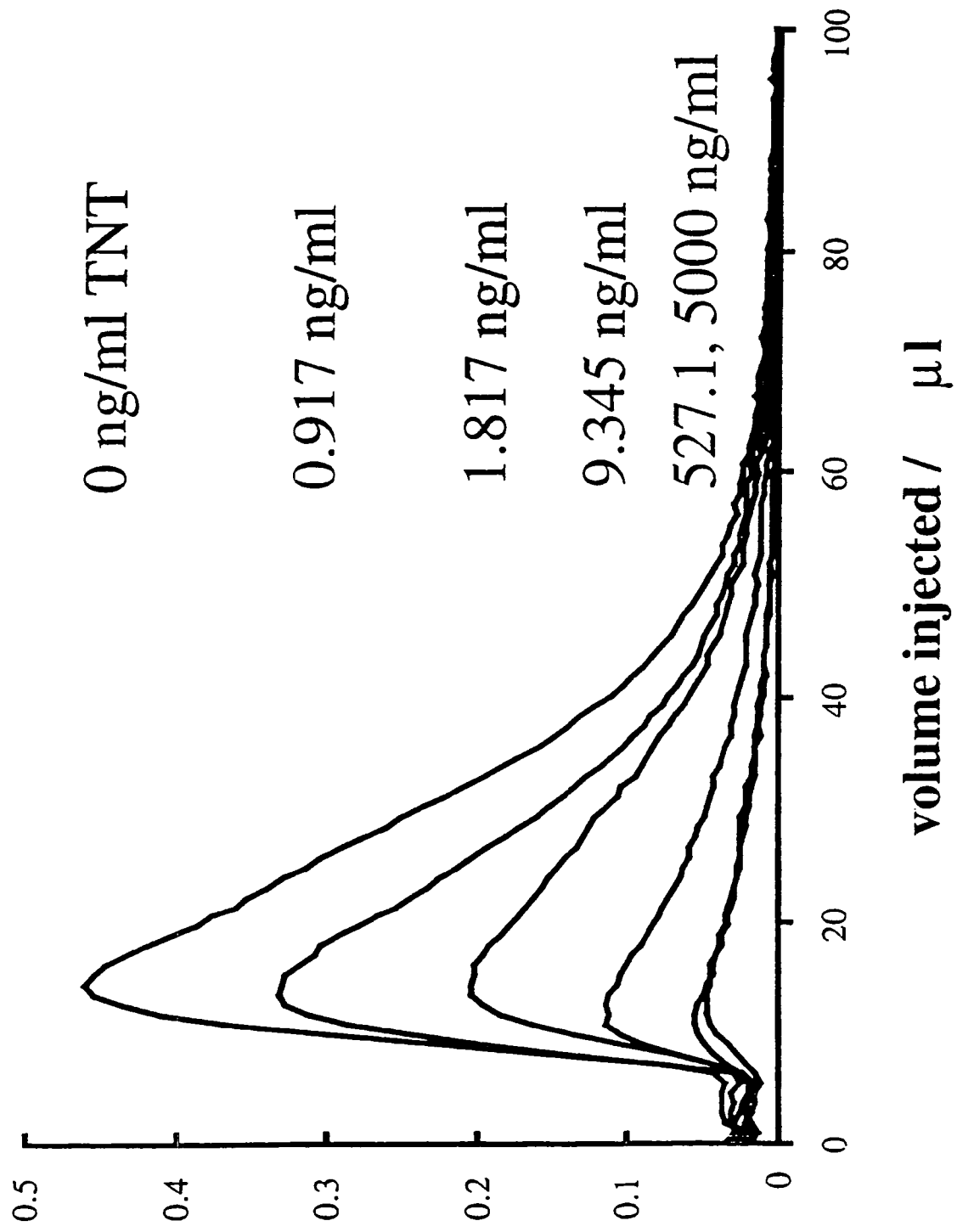
FIG. 10 is a plot of peaks for several standard concentrations of TNT as described in the Examples.

FIG. 10 shows peaks for several standard concentrations of TNT. In this competitive assay, no sample TNT leads to the largest peak and increasing TNT concentrations lead to smaller peaks. The 527 and 5000 ng/ml runs were not distinguishable and were taken as ∞ concentration. Note that the ∞ peak area was non-zero. Runs performed using buffer solution in place of TNT-HRP conjugate resulted in peak areas equal to the ∞ peak area of the semi-automated method, proving that the ∞ baseline was not due to residual enzyme activity. Particles contain iron species which should be responsible for some dye formation via the Fenton reaction in the color development solution that contained $H_2O_2$. There was no peak when buffer solution replaced particle suspension in a blank run.

Figure 11:
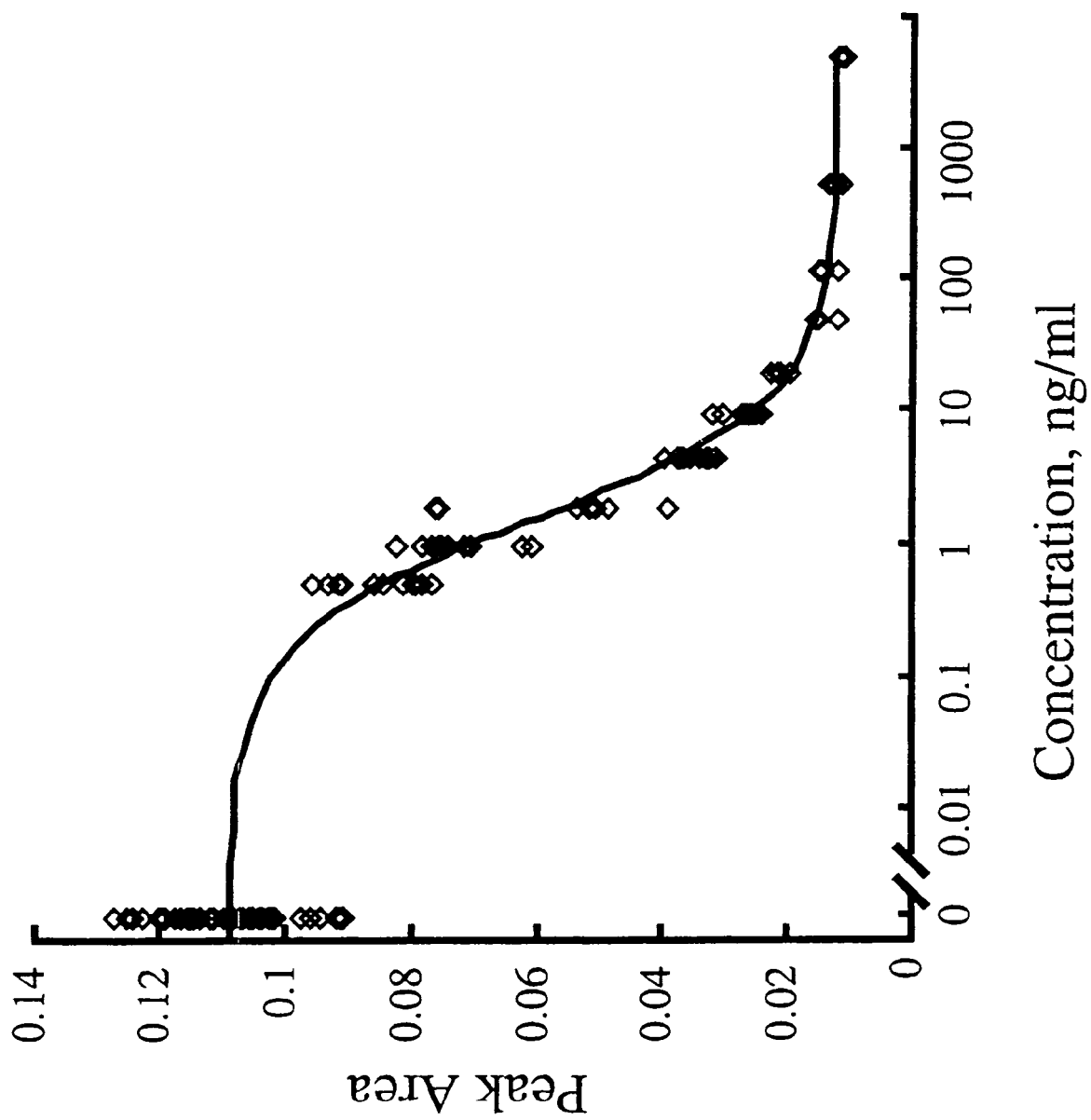
FIG. 11 is a plot of peak areas as a function of TNT standard concentration for 118 semi-automated procedure runs on 8 separate days over a time span of 43 days, as described in the Examples.

FIG. 11 shows peak areas as a function of TNT standard concentration for 118 semi-automated procedure runs on 8 separate days over a time span of 43 days. These illustrate the expected sigmoidal shape of the calibration curve and the stability of the calibration over a long time period.

The absorbency peak areas, B, for this type of immunoassay data are customarily fitted to one of the sigmoidal relationships in equations 1 and 2. Fare, T. L.; Sandberg, R. G.; Herzog, D. P.; "Considerations in immunoassay calibration"; In Environmental Immunochemical Methods; Emon, J. M. V., Gerlach, C. L., Johnson, J. C.; American Chemical Society: Washington, D.C., 1996; ACS Symposium Series 646; pp. 240-253.

$$B/B_o = \{1+(C/C_{0.5})^b\}^{-1} \quad (1)$$

$$(B-d)/(a-d) = \{1+(C/C_{0.5})^b\}^{-1} \quad (2)$$

The parameter $B_o$ gives the peak area of the blank, so $B/B_o$ is the sample to blank peak area ratio used as a measure of response. C is the sample concentration and $C_{0.5}$ is the concentration where $B/B_o$ is 50%. The parameter "b" is a fitting parameter related to the slope of the linear region of the curve. When the peak area at infinite concentration is nonzero, as is the case in FIG. 10, the relationship in equation 2 is used. The left side is a "corrected" $B/B_o$. The parameter "d" is the fitted value for the peak area of the infinite concentration peak and "a" is the fitted value for $B_o$. FIG. 11 plots the fitted curve for these data obtained using the semi-automated procedure.

Our results are in very reasonable agreement with the vendors, especially considering the recognized uncertainties in fitting sigmoidal calibration curves in immunoassays. Our procedure mixes antibody (on magnetic particles) and TNT-HRP conjugate in the same ratio as the vendors recommended procedure. Our fit gives a value of 1.51 ng/ml for the TNT concentration where the peak area is 50% of the blank peak area (corrected for the infinite concentration peak area), compared to a value of 1.44 in the vendor's literature. The TNT concentration where the peak area is 90% is 0.16 ng/ml, compared to 0.07 claimed by the vendor. The vendor uses this criterion to define a lower detection limit, as have others. C. S. Hottenstein, F. M. Rubio, D. P. Herzog, J. R. Fleeker and T. S. Lawruk, "Determination of trace atrazine levels in water by a sensitive magnetic particle-based enzyme immunoassay", J. Agric. Food Chem., 44(11), (1996) 3576-3581.

The standard deviations and relative standard deviations for each test concentration are given in Table 3.

TABLE 3

Standard deviations and relative standard deviations at test concentrations for the semi-automated approach.

| Concentration, Ng/ml | Average Peak Area, Absorbance | Standard Deviation, Absorbance | Relative Standard Deviation, % | Number of Points |
|---|---|---|---|---|
| Blank | 0.1087 | 0.0099 | 9.1 | 38 |
| 0.4681 | 0.0849 | 0.0057 | 6.7 | 14 |
| 0.917 | 0.0736 | 0.0049 | 6.7 | 12 |

TABLE 3-continued

Standard deviations and relative standard deviations at test concentrations for the semi-automated approach.

| Concentration, Ng/ml | Average Peak Area, Absorbance | Standard Deviation, Absorbance | Relative Standard Deviation, % | Number of Points |
|---|---|---|---|---|
| 1.817 | 0.0567 | 0.014 | 25 | 7 |
| 4.265 | 0.0350 | 0.0027 | 7.7 | 10 |
| 9.345 | 0.0270 | 0.0025 | 9.4 | 8 |
| 18.76 | 0.0212 | 0.00073 | 3.4 | 8 |
| 47.55 | 0.0143 | 0.0017 | 11.8 | 4 |
| 110.4 | 0.0138 | 0.0012 | 8.9 | 4 |
| 527.1 | 0.0120 | 0.00096 | 8.0 | 5 |
| 5000 | 0.0113 | 0.00048 | 4.3 | 5 |

Two standard deviations from the mean of replicate blank runs is another measure used for defining detection limits, C. S. Hottenstein, F. M. Rubio, D. P. Herzog, J. R. Fleeker and T. S. Lawruk, "Determination of trace atrazine levels in water by a sensitive magnetic particle-based enzyme immunoassay", J. Agric. Food Chem., 44(11), (1996) 3576-3581, and is reported to be an industry standard method. Deshpande, S. S. Enzyme Immunoassays: From Concept to Product Development; Chapman & Hall: New York, 1996, p. 323. The vast majority of our data for blank and standard runs is within two standard deviations of the mean. Using this criterion, our data yield a value of 0.4 ng/ml for the detection limit. It is again worth noting our results are based on data taken over 43 days, not replicate runs in a single day.

A 43 day reproducibility test is quite severe. For this TNT assay kit, the vendor reports % CV values within assays and between assays of 3-8% for 5 replicates on each of 5 days (25 samples), and specifies a % CV of 10%. % CV is the coefficient of variation (standard deviation/mean times 100), a term for relative standard deviation used in the immunoassay literature. Deshpande, S. S. Enzyme Immunoassays: From Concept to Product Development; Chapman & Hall: New York, 1996, p. 314. Our results (Table 3) with values typically 6 to 9% over 43 days are quite good and in reasonable agreement with vendor specifications. One concentration (1.8 ng/ml with a standard deviation of 25%) is clearly an outlier, while a couple of concentrations are at 3 to 4%. For additional comparison, in an ELISA assay for alachlor using an automated microplate system, Young et al. (Young, B. S.; Parsons, A.; Vampola, C.; Wang, H.; "Evaluation of an automated immunoassay system for quantitative analysis of atrazine and alachlor in water samples"; In Environmental Immunochemical Methods; Emon, J. M. V., Gerlach, C. L., Johnson, J. C.; American Chemical Society: Washington, D.C., 1996; ACS Symposium Series 646; pp 183-190) report % CV values ranging from 2 to 9% for duplicate standards on each of five days. For triplicate spiked Milli-Q water samples on five separate days, their % CV values were over 7%. % CV values of 5 to 10% for replicates over 5 days have been reported for a magnetic particle based immunoassay for atrazine. C. S. Hottenstein, F. M. Rubio, D. P. Herzog, J. R. Fleeker and T. S. Lawruk, "Determination of trace atrazine levels in water by a sensitive magnetic particle-based enzyme immunoassay", Journal of Agricultural and Food Chemistry, 44((1996) 3576-3581. We conclude that our precision over 43 days was very good.

Comparison to Manual Procedures

The procedure above was designed to work like the manual procedure, but with smaller reagent volumes and shorter reaction times. The ratio of antibodies to enzyme conjugate was the same as in the manual procedure, but we used 200 μL of particle suspension and 100 μL of TNT-HRP conjugate in contrast to volumes of 500 and 250 μL in the manual method. The incubation time and color development times of 4 minutes each are significantly shorter than the manual method procedure using a 15 minute incubation time and a 20 minute color development time. Our shorter times were sufficient to obtain adequate peak areas, while shorter times would not have significantly shortened overall analysis time.

Automation reduced variability due to inconsistencies that occur in manual procedures, such as, for example, incubation time and color development time. The present work shows that the semi-automated and automated procedures exhibit excellent results over a time period of 43 days.

Analysis of Color Development Data

Increasing color development time increases product generation as expected, as shown in the data for blank runs (under the standard reference semi-automated procedure) as a function of color development time in Table 4.

TABLE 4

Effect of Color Development Time

| Time, min | blank peak area, |
|---|---|
| 0.5 | 0.0157 |
| 1 | 0.0335 |
| 2 | 0.0647 |
| 4 | 0.109 |
| 8 | 0.196 |

One could obtain greater peak areas with longer development times, but there is no apparent advantage to doing so. It should be noted that in the manual procedure, 500 μL of color development solution are used, and this is diluted with an additional 500 microliter of stop solution. The colored product is evenly distributed in 1 ml. In the flow system, the magnetic particles with conjugated enzyme are located within a 22 microliter tubing zone and the colored peak passes through the optical cell in approximately 50 μL of pumped volume. Undoubtedly some dispersion occurs on going from the 0.02 inch tubing to the 1 mm (ca. 0.04 in) flow cell diameter. Thus, the colored product is at least 20 times more concentrated than in the manual procedure. In addition, we have observed that the blue colored product at neutral pH has a higher absorbency peak than the yellow form in acidic solution.

Increasing incubation time increases peak areas for both blank and standard samples, as shown in Table 5.

TABLE 5

Effect of Competitive Mix Incubation Time

| Time, min | Blank Peak Area, $B_o$ | Std Peak Area, B | $B/B_o$ |
|---|---|---|---|
| 0.5 | 0.0765 | 0.0289 | 0.378 |
| 1 | 0.0782 | 0.0308 | 0.394 |
| 2 | 0.0948 | 0.0351 | 0.370 |
| 4 | 0.109 | 0.0350 | 0.322 |
| 8 | 0.160 | 0.0470 | 0.294 |
| 16 | 0.224 | 0.0531 | 0.237 |

The response in terms of $B/B_o$ decreases somewhat with time at incubation times longer than 1 minute, as shown in Table 5. For example, for the 4.3 ng/ml sample used, the $B/B_o$ value changed from 0.32 to 0.29 from 4 to 8 minutes in these runs. The slope does not change from 4 to 16 minutes. Since the assay does not reach equilibrium within the vendor recommended 15 minute incubation time, the selection of competitive mixture time is somewhat arbitrary. Increasing use of nonequilibrium assays has been noted. Deshpande, S. S. Enzyme Immunoassays: From Concept to Product Development; Chapman & Hall: New York, 1996, p. 309. Failure to control the incubation time can influence the reproducibility of the analyses. In our semi-automated assay, the incubation period is automatically timed.

We examined a number of other factors that could influence the reproducibility of the calibrations. Shielding the color development solutions from light throughout the procedure made a measurable difference in analytical peak areas and was important for reproducibility. Room lighting was demonstrated to have an effect on assay baselines by photoreaction of the color development solution when optically clear tubing was used. The antibody-derivatized magnetic particles, TNT-enzyme conjugate, and color development reagent solutions were kept at 0° C. as a precaution, although this was not necessary. The reagent vendor actually states that the enzyme conjugate and particles must be allowed to reach room temperature before use. As a test, enzyme and antibody solutions were deliberately left at room temperature for 8.25 hours and used at room temperature. Peak areas for blank and 4.265 ng/ml TNT were well within the margin of error for the calibration repeatability runs to be described below and plotted in FIG. 11. (This figure actually contains these room temperature runs.)

Example Two

Cleaning of Apparatus Between Assays

Carryover cleaning. To eliminate carryover from one sample the next, the system was cleaned with acetone using the steps described in Table 2. This wash procedure takes two minutes.

TABLE 2

Sequential Injection Procedure for Cleaning Between Runs.

| | Procedural Step | Solution | Port | Volume, μl | Flow Rate, μl/s |
|---|---|---|---|---|---|
| 1 | Place acetone vial at mix inlet | | | | |
| 2 | Initialize mix inlet | Acetone | mix | | |
| 3 | Aspirate | Acetone | mix | 90 | 50 |
| 4 | Fill the cell | Acetone | cell | −85 | 200 |
| 5 | Aspirate | Acetone | mix | 450 | 50 |
| 6 | Remove acetone vial | | | | |
| 7 | Empty the inlet line | Acetone | mix | inletVol | 50 |
| 8 | Soak for 60 seconds | | | | |
| 9 | Discard through cell | Acetone | cell | −450 | 50 |
| 10 | Rinse the mix inlet | Wash | mix | −inletVol | 50 |
| 11 | Empty the inlet line | Wash | mix | inletVol | 50 |
| 12 | Rinse the cell | Wash | cell | −inletVol −150 | 200 |
| 13 | Restore the mix inlet | | | | |

The automated acetone cleaning procedure outlined in Table 2 was effective at removing TNT carryover from the semi-automated method up to and including the maximum tested concentration of 5000 ng/ml TNT. The carryover error without cleaning was characterized by running a sequence of standards followed by blanks: 9.3, blank, 110, blank, 527, blank, 5000 ng/ml, blank. Based on the resulting peak areas, the apparent concentrations of the blanks were 0.1, 0.6, 1.2, and 1.1 ng/ml. There was no measurable carryover using the acetone cleaning procedure.

Example Three

Methodology, Fully Automated Procedure

The automated method was the same as the semi-automated method except that mixing of sample and reagents was automated by pulling sample, particle suspension, and TNT-HRP solution as stacked zones into the holding coil. Zone volumes for sample, particles, and TNT-HRP were 10 µl, 15 µl, and 15 µl, respectively, and the zone stacking was repeated 10 times to yield the total solution volumes of 100, 150, and 150 µl. An important difference between the semi-automated and automated procedure is that in the automated procedure, free sample TNT is pulled into the flow system and can adsorb to tubing or valve surfaces. In the semi-automated procedure, the TNT has the opportunity to bind to the magnetic particles before being handled in the flow system.

The 3-part mixture was injected to the capture cell immediately after zone stacking. Therefore, the competitive assay incubation time of the automated method was defined by the time required for zone stacking plus the time needed for capture of particles at the magnet, which totaled 4.25 minutes. The total procedure required 15.8 minutes, beginning with aspirating the solutions into the holding coil, and ending with discarding the particles.

Calibration Stability Test—Automated Procedure

Figure 12:
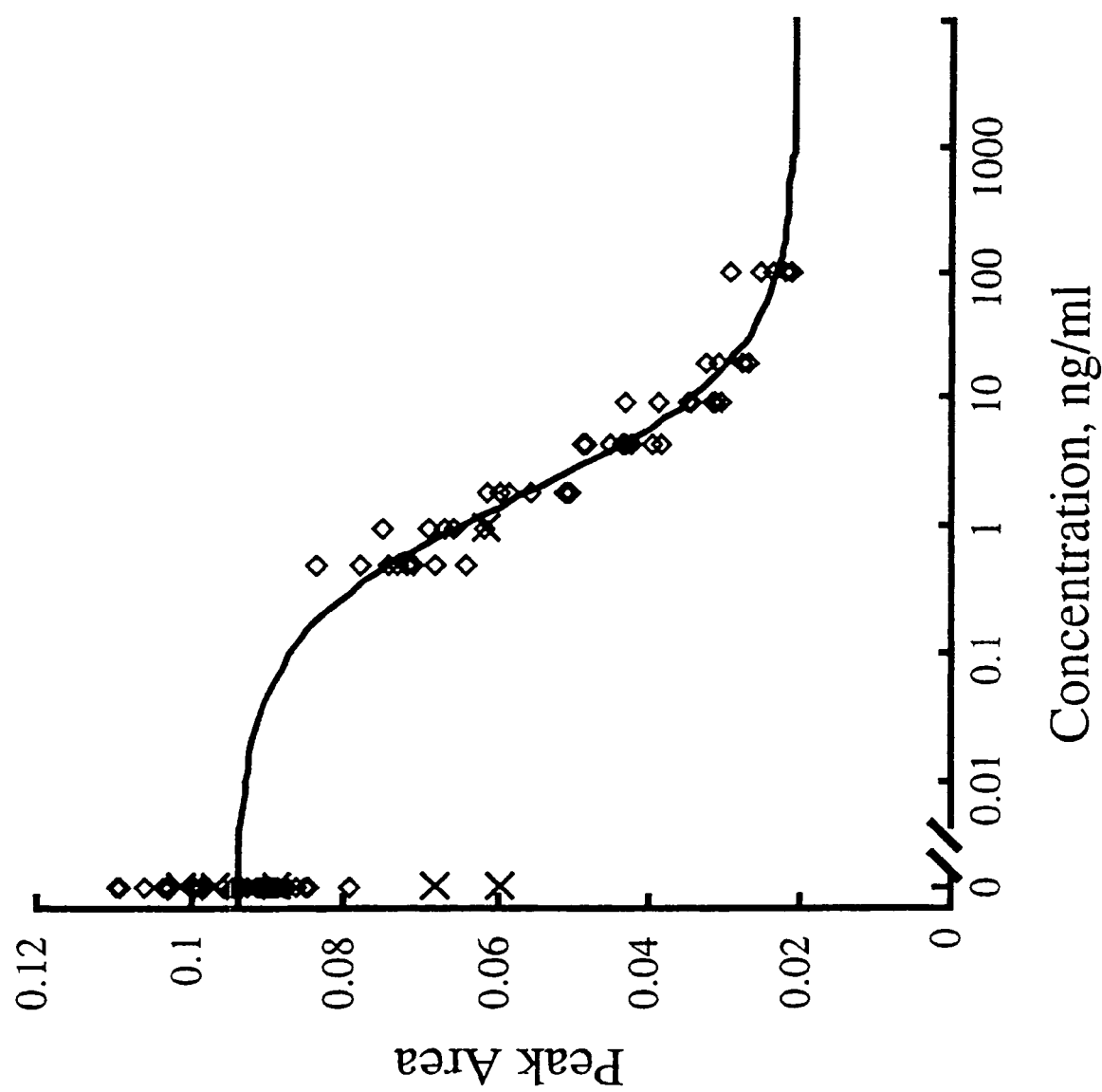
FIG. 12 is a plot of automated calibration data as described in the Examples.

To evaluate the automated procedure and test the calibration stability, 83 calibration standards from blank to 100 ng/ml were run by the automated procedure over a time-span of 14 days. These automated calibration data are shown in FIG. 12.

The calibration was essentially stable for the two week test period, but carryover after some tests at the highest test concentration, 100 ng/ml, was apparent in lower than expected results for the next standard. These points are included in FIG. 12 with "X" markers on the plot, where they are particularly notable for blanks run after the 100 ng/ml standard. These points were not included in the statistics.

In tests without cleaning, 100 ng/mL caused a carryover effect in a subsequent blank, but lower concentrations did not. The automated procedure was run using DNA-zap, rather than acetone, as the cleaning solution, and this did not prevent carryover problems at 100 ng/ml. (DNA Zap™ is a two-part reagent that is harmless before mixing and after reaction, which makes it very attractive as a flow system cleaning agent. It is a proprietary formulation for destroying DNA contamination on surfaces prior to polymerase chain reaction amplification by cleaving of phosphate-sugar linkages.)

At the end of the two week calibration set, a 5000 ng/mL standard was run and this caused persistent carryover that could not be removed with either DNA-zap or acetone cleaning. Dismantling and cleaning the valve was necessary to resolve this carryover. This stands in stark contrast to the semi-automated method where 5000 ng/mL standards could be run routinely with acetone cleaning, and produced only 1.1 ng/mL apparent TNT concentration in a subsequent blank run without cleaning.

During method development, an aqueous mixture of 0.3 M KOH and 0.03 M $Na_2SO_3$ was used at least 96 times in order to eliminate TNT carryover by forming soluble anionic TNT adducts with hydroxide and sulfite. This method was generally satisfactory, but the acetone procedure that replaced it was more reliable.

Example Four

Particle Capture and Resuspension Evaluation

Particle capture was evaluated by passing a 50 µl zone of particle suspension at various flow rates through the magnetic capture zone and measuring absorbance downstream. Relative to the peak area with no magnet present, the turbidity peak areas were 0.6% at 2.5 µl/s, 7% at 5 µl/s, and 60% at 10 µl/s after correcting for the flow rate changes. Thus, 99% of the magnetic particles were captured at 2.5 µl/s. The repeatability of particle capture and release is apparent in the calibration stability results to be described below.

Sudden changes in flow rate from zero to 200 µl/s were used to displace captured particles from the magnetic cell tubing wall. Both 200 and 400 µl/s flow rates were found to be effective for particle release, as determined by having no carryover enzyme-activity in subsequent blank runs. However, 200 µl/s disperses the particles less than a 400 µl/s pulse, and was preferred. Particle release was carried out in two directions. After completion of the assay, particles were released to travel forward through the transmittance optical cell and discarded. During the procedure, particles were released with either a 5 or 15 µL pulse at 200 µL/s back toward the valve to resuspend them in the 22 µL zone between the magnet and the valve. This procedure was particularly useful for suspending the particles in the reagent solution for color development, but it was also used in the wash steps. After color development, the particles were recaptured in the capture zone as the solution was pushed through the optical transmittance cell at 1 µL/s. Resuspending particles provides better surface accessibility for wash and catalysis steps than leaving the particles in a layer against the magnetic cell wall. In addition, resuspension prevents particle aggregates from forming, which can be a problem if the magnetic particles are left in the magnetic zone too long. This is why particles were resuspended with a 5 microliter pulse in steps 4 and 10 of Table 1, just before the air segment discard and color inlet initialization steps. Air segments were used to separate the solutions pulled into the holding coil (competitive mix and color development reagent solution) as described above.

Example Five

Alternative Procedures

Two other approaches were considered. In one the unlabeled analyte was added first, a sequential approach that is sometimes used to increase sensitivity. Deshpande, S. S. Enzyme Immunoassays: From Concept to Product Development; Chapman & Hall: New York, 1996, p. 309. When a 4.265 ng/ml TNT standard was incubated for 16 minutes with antibody particles prior to addition of the TNT-HRP, the resulting peak area was the same as if the 3 reagents were mixed without the added incubation. The peak area predicted 4.3 ng/ml for this altered 4.265 ng/ml run.

In the converse experiment, particles were incubated with TNT-HRP, washed three times, and incubated with TNT. The color development portion of the assay was used as a measure of the bound TNT-HRP remaining after incubation. Displacement of TNT-HRP was significant only in the μg/ml range when TNT standard was incubated for 16 minutes. A 5000 ng/ml TNT standard resulted in 71.7% of the blank peak area (average of triplicate runs). In competitive assays, this concentration represented infinite TNT concentration, completely eliminating HRP activity in the color development step.

An alternative experiment was conducted where atrazine-HRP conjugate (also from Strategic Diagnostics) was used in a blank run in place of TNT-HRP, yielding a blank peak area 17% that of the TNT-HRP area resulted. These results indicate that the antibody-coated magnetic particles can also bind atrazine-HRP, suggesting that there may be some affinity for HRP regardless of the conjugated analyte or analyte-analog.

All references, including publications, patents, and patent applications, cited or listed in this specification are herein incorporated by reference as if each individual reference were specifically and individually indicated to be incorporated by reference and set forth in its entirety herein. Further, any theory, proposed mechanism of operation, or finding stated herein is meant to further enhance understanding of the present invention, and is not intended to in any way limit the present invention to such theory, proposed mechanism of operation, or finding.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A method comprising:
providing a fluid flow path, the fluid flow path having first and second ends, a fluid flow controller effective to variably impose a positive or negative pressure on the flow path to cause controlled fluid flow through the fluid flow path in a first or second direction at predetermined rates, and a capture zone between the first and second ends, wherein a fixed magnetic field intercepts the fluid flow path in the capture zone;
providing in the fluid flow path a first mixture including a plurality of solid magnetic particles dispersed in a carrier medium;
passing the first mixture through the capture zone at a first predetermined capture rate whereby a major portion of the magnetic particles become trapped in the capture zone by the force of the magnetic field and thereby separated from the carrier medium to form a first magnetic particle isolate;
perfusing the first magnetic particle isolate with a first dispersion medium; and
pulsing the first dispersion medium through the capture zone at a first predetermined dispersion rate effective to dislodge the first magnetic particle isolate from the capture zone, move the magnetic particles from the magnetic field, and suspend the magnetic particles in the first dispersion medium to provide a second mixture.

2. The method in accordance with claim 1 wherein the fixed magnetic field has a strength that is substantially constant during said passing of the first mixture, said perfusing, said pulsing and said passing of the second mixture.

3. The method in accordance with claim 1 wherein the fixed magnetic field is provided by a permanent magnet having a fixed relationship to the fluid flow path.

4. The method in accordance with claim 1 wherein the fixed magnetic field is provided by an electromagnet that has a fixed relationship to the fluid flow path and a that produced a fixed magnetic field.

5. The method in accordance with claim 1 wherein the magnetic particles include a surface-bound selective agent featuring selective affinity for a target substance.

6. The method in accordance with claim 5 wherein the magnetic particles with surface-bound selective agents are effective to selectively retain a chemical or biological species in a sample.

7. The method in accordance with claim 1 wherein the magnetic particles include properties suitable for adsorption of multiple target substances via a non-specific interaction.

8. The method in accordance with claim 7 wherein the non-specific interaction is selected from the group consisting of an electrostatic interaction, a van der Waals interaction, dipole-dipole interaction and a hydrogen bonding interaction.

9. The method in accordance with claim 6 wherein the first dispersion medium includes the sample.

10. The method in accordance with claim 6 wherein the selective agent is effective to retain a biological species in a sample, and wherein the selective agent is selected from the group consisting of an antigen, an antibody, a protein receptor, a ligand, an oligonucleotide, streptavidin, avidin, biotin and lectin.

11. The method in accordance with claim 10 wherein the selective agent is an antibody.

12. The method in accordance with claim 6, wherein the sample includes an analyte sample for an ELISA assay; wherein the selective agent is an antibody that selectively retains the analyte; and wherein the sample further includes an analyte-enzyme conjugate.

13. The method in accordance with claim 12, wherein the analyte-enzyme conjugate comprises an enzyme having a specific catalytic activity and specificity for an analysis reagent.

14. The method in accordance with claim 6 wherein the carrier medium includes the sample.

15. The method in accordance with claim 14 wherein the mixture is incubated for a first period of time effective to cause the selective agent to contact and retain the species.

16. The method in accordance with claim 15 wherein the first dispersion medium is a first wash solution.

17. The method in accordance with claim 16, further comprising passing the second mixture through the capture zone at a second predetermined capture rate at which rate a major portion of the magnetic particles become trapped in the capture zone by the force of the magnetic field and thereby removed from the first dispersion medium to form a second magnetic particle isolate.

18. The method in accordance with claim 17, further comprising:
perfusing the second magnetic particle isolate with a second dispersion medium; and
pulsing the second dispersion medium through the capture zone at a second predetermined dispersion rate effective to dislodge the second magnetic particle isolate from the capture zone, move the magnetic particles from the magnetic field, and suspend the magnetic particles in the second dispersion medium to provide a third mixture.

19. The method in accordance with claim 18 wherein the second dispersion medium comprises an analysis reagent.

20. The method in accordance with claim 19, further comprising passing the third mixture through the capture zone at a third predetermined capture rate at which rate a major portion of the magnetic particles become trapped in the capture zone by the force of the magnetic field and thereby removed from the second dispersion medium to form a third magnetic particle isolate.

21. The method in accordance with claim 20 wherein the flow path further includes a detection zone, and wherein a detector is positioned to detect a physical or chemical property of a fluid in the detection zone; and further comprising, after passing the third mixture through the capture zone, detecting a physical or chemical property of a member selected from the group consisting of the second dispersion medium and the third magnetic particle isolate.

22. The method in accordance with claim 21 wherein the analysis reagent is a coloring agent; and wherein the detector is an optical detector.

23. The method in accordance with claim 22, further comprising: passing the second dispersion medium through the detection zone; and measuring the property of the second dispersion medium.

24. The method in accordance with claim 18 wherein the second dispersion medium comprises a second wash solution.

25. The method in accordance with claim 24, further comprising passing the third mixture through the capture zone at a third predetermined capture rate at which rate a major portion of the magnetic particles become trapped in the capture zone by the force of the magnetic field and thereby removed from the second dispersion medium to form a third magnetic particle isolate.

26. The method in accordance with claim 25, further comprising:
  perfusing the third magnetic particle isolate with a third dispersion medium; and
  pulsing the third dispersion medium through the capture zone at a third predetermined dispersion rate effective to dislodge the third magnetic particle isolate from the capture zone, move the magnetic particles from the magnetic field, and suspend the magnetic particles in the third dispersion medium to provide a fourth mixture.

27. The method in accordance with claim 26, further comprising passing the fourth mixture through the capture zone at a fourth predetermined capture rate at which rate a major portion of the magnetic particles become trapped in the capture zone by the force of the magnetic field and thereby removed from the third dispersion medium to form a fourth magnetic particle isolate.

28. The method in accordance with claim 27 wherein the flow path further includes a detection zone, and wherein a detector is positioned to detect a physical or chemical property of a fluid in the detection zone; and further comprising, after passing the fourth mixture through the capture zone, detecting a physical or chemical property of a member selected from the group consisting of the third dispersion medium and the fourth magnetic particle isolate.

29. The method in accordance with claim 28 wherein the second dispersion medium comprises an analysis reagent.

30. The method in accordance with claim 29 wherein the analysis reagent is a coloring agent; and wherein the detector is an optical detector.

31. The method in accordance with claim 1 wherein the magnetic field has a field gradient in the capture zone of from about 0.1 to about 2 kGauss/cm.

32. The method in accordance with claim 1 wherein the flow path has a volume of from about 0.01 to about 50 µL.

33. The method in accordance with claim 1 wherein the flow path has an average diameter of from about 0.001 to about 5 mm.

34. The method in accordance with claim 1 wherein the first predetermined capture rate is from about 1.0 to about 13 mm/s.

35. The method in accordance with claim 1 wherein the first predetermined dispersion rate is from about 250 to about 2500 mm/s.

36. The method in accordance with claim 1 wherein the flow path is a microchannel.

37. The method in accordance with claim 1 wherein said passing of the first mixture comprises passing in a first direction; wherein said perfusing the first dispersion medium comprises passing in a second direction opposite the first direction; and wherein said pulsing the first dispersion medium through the capture zone comprises pulsing in the first direction.

38. The method in accordance with claim 1 wherein the flow controller comprises:
  a multiport selection valve including a primary port and a plurality of secondary ports, wherein a first secondary port is fluidly connected to the inlet of the fluid flow path;
  a holding coil having a proximal end and a distal end; wherein the distal end is fluidly connected to the primary port of the selection valve;
  a three-way valve having a first port fluidly connected to the proximal end of the holding coil; a second port fluidly connected to a variable speed reversible pump; and a third port fluidly connected to a source of a wash composition.

39. The method in accordance with claim 38 wherein the variable speed reversible pump is a stepper-motor-driven syringe pump.

40. The method in accordance with claim 38 wherein the multiport selection valve, the three-way valve and the pump are controlled by a pre-programmed computer.

41. The method in accordance with claim 1, wherein the flow path in the capture zone is substantially free from fixed magnetizable solid matrix structures.

42. A method comprising:
  passing a mixture including a plurality of solid magnetic particles dispersed in a carrier medium through a conduit extending through a fixed magnetic field at a first predetermined capture rate whereby magnetic particles become trapped in the field and thereby separated from the carrier medium to form a magnetic particle isolate;
  passing a dispersion medium into the conduit and into contact with the magnetic particle isolate; and
  pulsing the dispersion medium through the conduit at a first predetermined dispersion rate effective to move the magnetic particles from the magnetic field and suspend the magnetic particles in the dispersion medium.

43. A method comprising:
  passing a first mixture including a plurality of solid magnetic particles dispersed in a carrier medium through a conduit extending through a magnetic field at a first predetermined capture rate whereby magnetic particles become trapped in the field and thereby separated from the carrier medium to form a magnetic particle isolate;
  releasing the magnetic particle isolate from the magnetic field by pulsing a dispersion medium through the conduit at a first predetermined dispersion rate effective to move the magnetic particles from the magnetic field and suspend the magnetic particles in the dispersion medium to provide a second mixture; and recapturing the magnetic particles by passing the second mixture through the magnetic field in a direction opposite said passing of the first mixture, at a second predetermined capture rate whereby magnetic particles become trapped in the field and thereby separated from the carrier medium to form a magnetic particle isolate.

44. The method in accordance with claim 43 wherein the first mixture has a different composition than the second mixture.

* * * * *